United States Patent
Alma et al.

(10) Patent No.: US 11,213,548 B2
(45) Date of Patent: *Jan. 4, 2022

(54) MODULATABLE SWITCH FOR SELECTION OF DONOR MODIFIED CELLS

(71) Applicants: CSL Behring Gene Therapy, Inc., Pasadena, CA (US); CSL Gene Therapy Pty Ltd., Parkville (AU)

(72) Inventors: Christopher Walter Alma, Castle Hill (AU); Jeffrey Bartlett, Columbus, OH (US); Louis Randall Breton, Tucson, AZ (US); Geoffrey Phillip Symonds, Rose Bay (AU); Ming Yan, Encino, CA (US)

(73) Assignees: CSL Behring Gene Therapy, Inc., Pasadena, CA (US); CSL Gene Therapy Pty Ltd., Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/538,818

(22) Filed: Aug. 12, 2019

(65) Prior Publication Data

US 2020/0038444 A1 Feb. 6, 2020

Related U.S. Application Data

(63) Continuation of application No. 16/038,643, filed on Jul. 18, 2018, now Pat. No. 10,426,798.

(60) Provisional application No. 62/533,707, filed on Jul. 18, 2017.

(51) Int. Cl.
| | | |
|---|---|---|
| A61K 35/17 | (2015.01) | |
| A61K 35/28 | (2015.01) | |
| A61P 37/06 | (2006.01) | |
| A61P 35/02 | (2006.01) | |
| C12N 5/0783 | (2010.01) | |
| A61K 35/12 | (2015.01) | |
| A61K 31/52 | (2006.01) | |

(52) U.S. Cl.
CPC .............. *A61K 35/17* (2013.01); *A61K 35/28* (2013.01); *A61P 35/02* (2018.01); *A61P 37/06* (2018.01); *C12N 5/0637* (2013.01); *A61K 31/52* (2013.01); *A61K 2035/124* (2013.01)

(58) Field of Classification Search
CPC .................................................... A61K 35/17
See application file for complete search history.

(56) References Cited

U.S. PATENT DOCUMENTS 10,426,798 B2 * 10/2019 Alma ................ A61P 37/06
2016/0361359 A1 * 12/2016 Valton ................ A61K 35/17

OTHER PUBLICATIONS

Guitart et al. (Arch Dermatol. 2002; 138: 1359-1365). (Year: 2002).*
Arguelles et al. (Leukemia and Lymphoma. 2001, vol. 42(1-2). pp. 145.150). (Year: 2001).*
Choudhary R, Baturin D, Fosmire S, Freed B, Porter CC (2013) Knockdown of HPRT for Selection of Genetically Modified Human Hematopoietic Progenitor Cells. PLoS ONE 8(3): e59594. doi:10.1371/journal.pone.0059594 (Year: 2013).*

* cited by examiner

*Primary Examiner* — Scott Long
(74) *Attorney, Agent, or Firm* — Charney IP Law LLC; Thomas M. Finetti

(57) ABSTRACT

The disclosed methods are generally directed to preventing, treating, suppressing, controlling or otherwise mitigating side effects of T-cell therapy, the T-cell therapy designed to accelerate immune reconstitution, induce a GVM effect, and/or target tumor cells.

25 Claims, 18 Drawing Sheets

Specification includes a Sequence Listing.

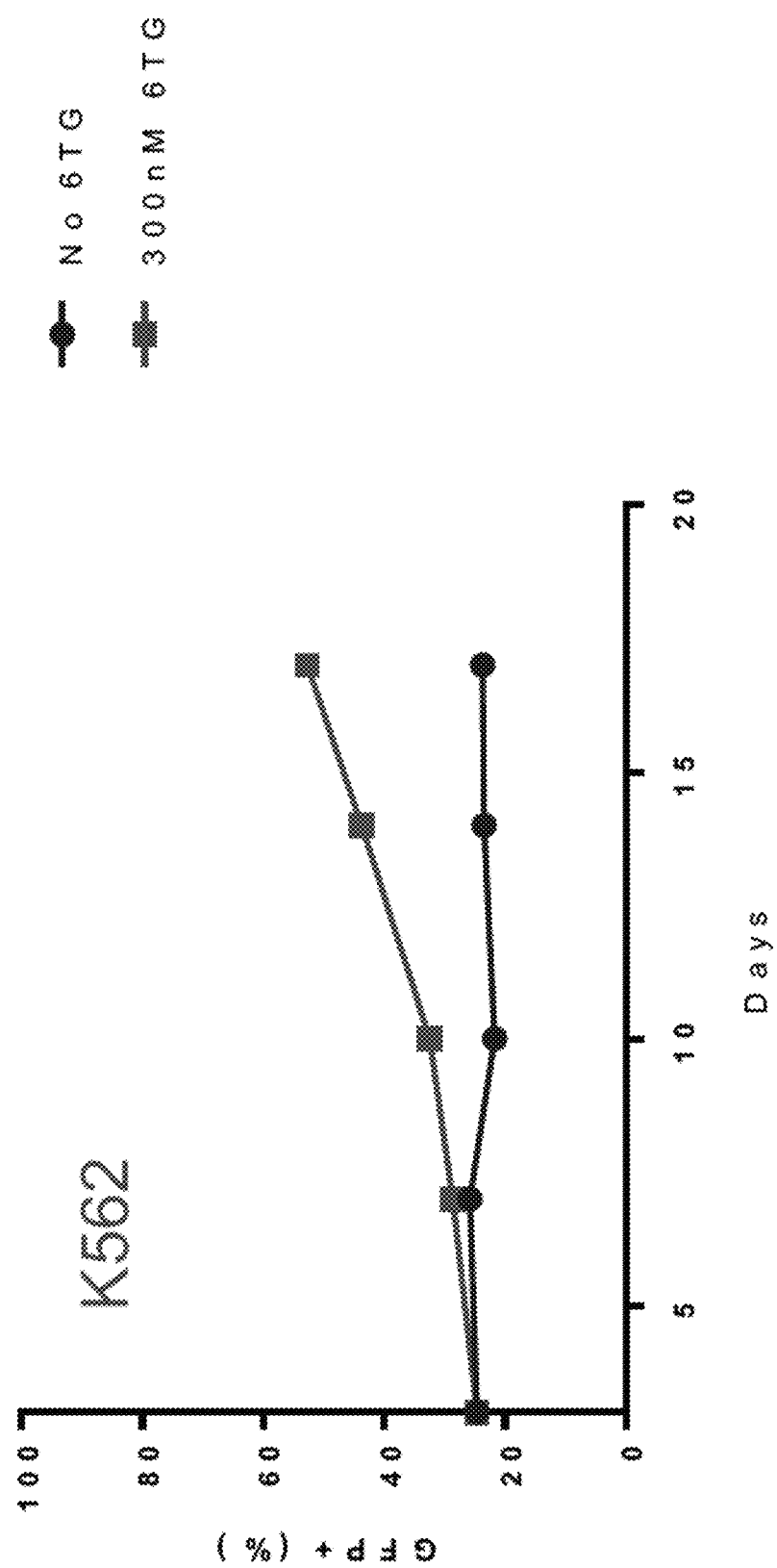

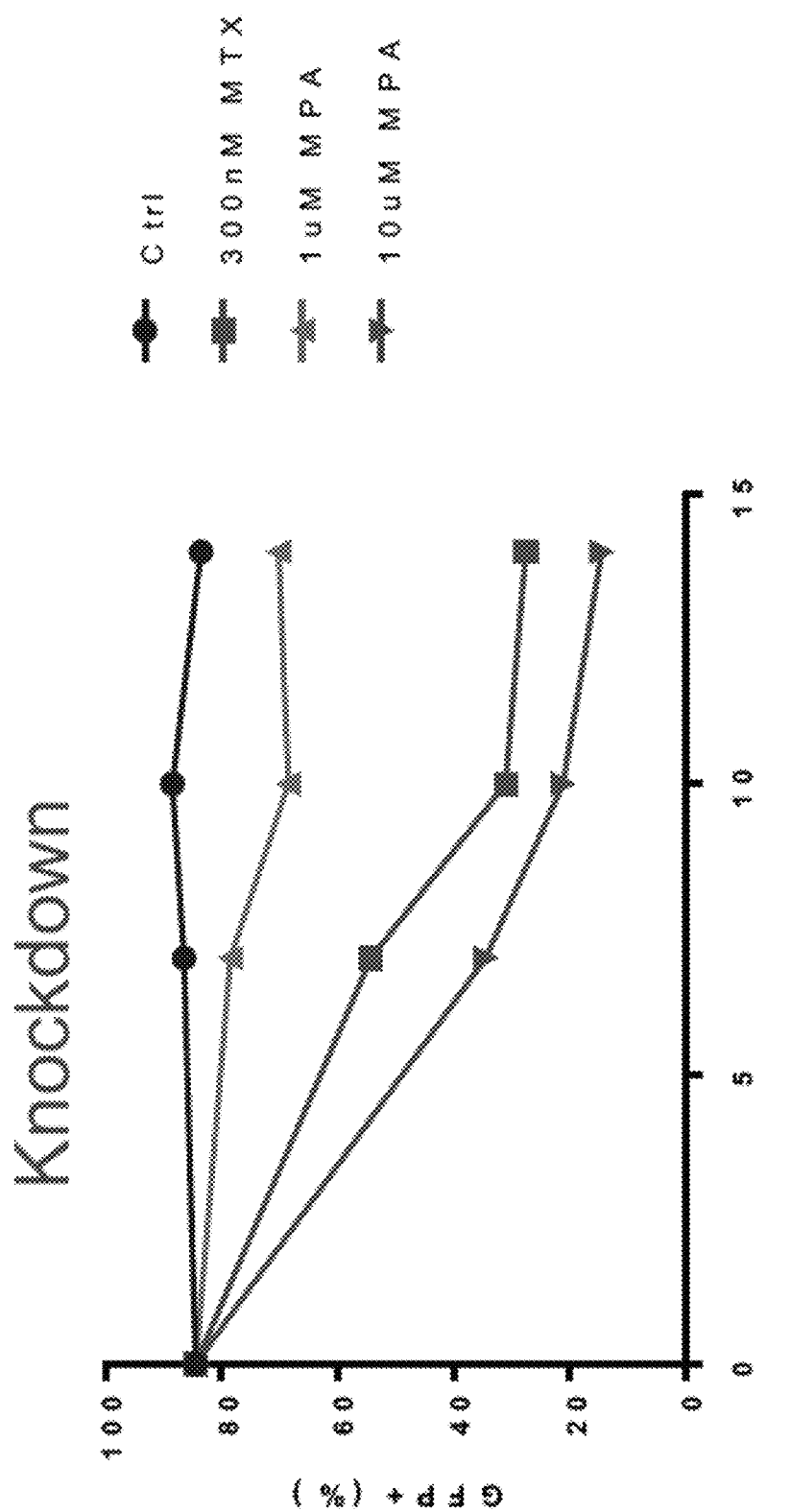

SEQUENCE LISTING

```
<160> NUMBER OF SEQ ID NOS: 1

<210> SEQ ID NO 1
<211> LENGTH: 92
<212> TYPE: DNA
<213> ORGANISM: Artificial Sequence
<220> FEATURE:
<223> OTHER INFORMATION: Synthetic: shRNA to knockout HPRT

<400> SEQUENCE: 1
aggatatgcc cttgactatt tgtccgacat agtcaagggc atatcctcct atacgggaac     60
tgataaacag gctgtatcag ttcccgtata gg                                   92
```

MODULATABLE SWITCH FOR SELECTION OF DONOR MODIFIED CELLS

CROSS REFERENCE TO RELATED APPLICATIONS

The present application claims the benefit of the filing date of U.S. patent application Ser. No. 16/038,643, filed on Jul. 18, 2018, which application claims the benefit of the filing date of U.S. Provisional Patent Application No. 62/533,707 filed on Jul. 18, 2017, the disclosures of which are each hereby incorporated by reference herein in their entireties.

FIELD OF DISCLOSURE

This disclosure generally relates to the fields of molecular biology and, in particular, vectors and host cells transduced by vectors.

BACKGROUND OF THE DISCLOSURE

Use of an allogeneic stem cell transplant (allo-SCT) as a therapeutic option for otherwise lethal diseases is continuously increasing. However, graft-versus-host disease (GVHD) remains a major complication of allo-SCT, affecting up to about 40-60% of allo-SCT patients. It is believed that GVHD occurs when immune competent cells, namely, T-lymphocytes, recognize membrane antigens on the host cells. These membrane antigens include a set of host polypeptides such as major and minor histocompatibility antigens displayed by the human leukocyte antigen system. The polymorphism of these polypeptides is believed to trigger T-cell activation and ultimately tissue injury through a variety of cellular effector mechanisms. The activation of the donor immune cells is augmented also by cytokines released from the site of tissue injury associated with the intense conditioning regimen ("cytokine storm").

Acute GVHD (aGVHD) usually occurs in the first 100 days after transplantation, whereas onset of chronic GVHD (cGVHD) is observed later. Changes in the onset period of both acute and chronic GVHDs have been observed, with acute cases occurring about 100 days after transplantation and chronic cases noticed earlier than usual. These changes from traditional patterns of acute and chronic GVHD were observed especially in the context of reduced conditioning intensity and use of peripheral blood as a stem cell source. As used herein, the term "GVHD" encompasses both acute and chronic graft-versus-host-disease.

The goal of hematopoietic progenitor cell or stem cell transplantation (HSCT) is to achieve the successful engraftment of donor cells within a recipient host, such that immune and/or hematopoietic chimerism results. Such transplants typically are used in the treatment of disorders such as leukemia, bone marrow failure syndromes, and inherited disorders (e.g., sickle cell anemia, thalassemia, immunodeficiency disorders, and metabolic storage diseases such as mucopolysaccharidosis), as well as low-grade lymphoma. Chimerism is the reconstitution of the various compartments of the recipient's hematoimmune system with donor cell populations bearing major histocompatibility complex (MHC) molecules derived from an allogeneic or xenogeneic donor, and a cell population derived from the recipient or, alternatively, the recipient's hematoimmune system compartments which can be reconstituted with a cell population bearing MHC molecules derived from only the allogeneic or xenogeneic marrow donor. Chimerism may vary from 100% (total replacement by allogenic or xenogeneic cells) to low levels detectable only by molecular methods. Chimerism levels may vary over time and be permanent or "temporary."

Donor leukocyte infusion's (DLI) have been used after allotransplant to treat relapsed or residual disease, to convert mixed to full donor chimerism, to restore full immune function as an 'add-back' after T-cell-depleted transplants and as a prophylaxis against relapse as preemptive therapy. The major complications after DLI include acute and chronic GVHD and infections associated with marrow aplasia or the use of immunosuppression. In most trials, up to about 60% of evaluable recipients of DLI develop GVHD. GVHD correlates with GVT activity and response in some but not all studies.

Over the years, several methods for GVHD prophylaxis and treatment have been proposed, such as immunosuppressive medications, graft engineering, and cellular therapies. Indeed, there exist several approaches to minimizing GVHD after DLI to prevent or mitigate post-transplant immune deficiency or to induce graft-versus-malignancy (GVM) in residual or recurring disease. For example, one approach that appears to minimize GVHD involves administration of low-dose DLI followed by dose escalation. The conventional approach to DLI has been to infuse single "bulk" doses containing variable numbers of CD3+ T cells, but this is believed to be associated with significant incidences of acute and chronic GVHD and occasionally with death. On the other hand, transfusion of donor lymphocytes in multiple aliquots, starting at low cell numbers and escalating the dosage at variable intervals as required may reduce the incidence of GVHD. (see Mackinnon S, Papadopoulos E B, Carabasi M H, et al. Adoptive immunotherapy evaluating escalating doses of donor leukocytes for relapse of chronic myeloid leukemia after bone marrow transplantation: separation of graft-versus-leukemia responses from graft-versus-host disease. Blood. 1995; 86:1261-1268). The assumption underlying the use of an escalating dose regimen is that the incidence of GVHD increases with the total cell dose administered. Thus, it is believed that identification of the minimal cell dose capable of inducing remission would reduce the risk for GVHD.

Alternatively, it is believed that GVHD may be reduced through depletion of CD8+ lymphocytes, which are thought to include most of the cells responsible for mediating GVHD (i.e. depletion of GVH effector cells). Outcomes suggest that graft-versus-leukemia activity can be retained with minimal GVHD. In small numbers of patients, the majority of responses have been sustained, although the overall clinical impact of this approach will require direct comparison to unmanipulated DLI.

It is also believed that GVHD may be reduced through inactivation of GVHD effector cells. Indeed, irradiated donor T-cell DLI is based on the hypothesis that the cells would induce GVM effects at the time of infusion but could not proliferate in response to allo-antigens. In addition, the use of donor T-cells expressing the herpes simplex thymidine kinase gene followed by ganciclovir treatment was studied for its effects pertaining to the modulation of alloreactivity occurring after bone marrow transplantation.

Calcineurin inhibitors and methotrexate (MTX) combination therapy has been used successfully to reduce the incidence and severity of GVHD and is the standard of care for GVHD prophylaxis. MTX, one of the earliest drugs used for GVHD prophylaxis, is believed to inhibit dihydrofolate reductase and production of thymidylate and purines, thereby suppressing T-cell response and proliferation as well as expression of adhesion molecules.

Although some of these strategies are effective in reducing the incidence of GVHD, these strategies often associate with a significant reduction in the GVM effect, thus jeopardizing the overall efficacy of HSCT.

BRIEF SUMMARY OF THE DISCLOSURE

In one aspect of the present disclosure is a method of providing benefits of a lymphocyte infusion to a patient in need of treatment thereof while mitigating side effects comprising: generating HPRT deficient lymphocytes from a donor sample; positively selecting for the HPRT deficient lymphocytes ex vivo to provide a population of modified lymphocytes; administering an HSC graft to the patient; administering the population of modified lymphocytes to the patient following the administration of the HSC graft; and optionally administering MTX if the side effects arise.

In some embodiments, the HPRT deficient lymphocytes are generated through knockdown of the HPRT gene. In some embodiments, the HPRT deficient lymphocytes are generated through knockout of the HPRT gene. In some embodiments, the positive selection comprises contacting the generated HPRT deficient lymphocytes with a purine analog (e.g. 6-thioguanine (6TG), 6-mercaptopurine (6-MP), or azathiopurine (AZA)). In some embodiments, the positive selection comprises contacting the generated HPRT deficient lymphocytes with a purine analog and a second agent. In some embodiments, the purine analog is 6TG. In some embodiments, an amount of 6TG is between about 1 to about 15 μg/mL. In some embodiments, the HSC graft is administered to the patient following myeloablative conditioning. In some embodiments, the modified lymphocytes are administered as a single bolus. In some embodiments, the modified lymphocytes are administered as multiple doses. In some embodiments, each dose comprises between about $0.1 \times 10^6$ cells/kg to about $240 \times 10^6$ cells/kg. In some embodiments, a total dosage of modified lymphocytes comprises between about $0.1 \times 10^6$ cells/kg to about $730 \times 10^6$ cells/kg. In some embodiments, the administration of the modified lymphocytes takes place 1 to 14 days after the administration of the HSC graft. In some embodiments, the administration of the modified lymphocytes takes place 2 to 4 weeks after the administration of the HSC graft. In some embodiments, the administration of the modified lymphocytes takes place contemporaneously with the administration of the HSC graft. In some embodiments, the MTX is optionally administered upon diagnosis of GVHD. In some embodiments, an amount of MTX administered ranges from about 2 mg/m$^2$/infusion to about 8 mg/m$^2$/infusion. In some embodiments, the MTX is administered in titrated doses.

In another aspect of the present disclosure is a method of treating cancer (e.g. a hematological cancer) in a patient in need of treatment thereof comprising: generating HPRT deficient lymphocytes from a donor sample; positively selecting for the HPRT deficient lymphocytes ex vivo to provide a population of modified lymphocytes; inducing at least a partial graft versus malignancy effect by administering an HSC graft to the patient; administering the population of modified lymphocytes to the patient following the detection of residual disease or disease recurrence; and optionally administering at least one dose of MTX to suppress at least one symptom of GVHD. In some embodiments, an amount of MTX administered ranges from about 2 mg/m$^2$/infusion to about 8 mg/m$^2$/infusion. In some embodiments, the MTX is administered in an amount to maintain at least some of the GVM effect.

In another aspect of the present disclosure is a method of treating cancer in a patient in need of treatment thereof comprising: generating CAR-T cells that include an antitumor chimeric receptor and which are HPRT deficient; positively selecting for the HPRT deficient CAR-T cells ex vivo to provide a population of CAR-T cells for administration; administering the population of CAR-T cells to the patient; and optionally administering at least one dose of MTX to suppress at least one symptom of GVHD or cytokine release syndrome. In some embodiments, the HPRT deficient CAR-T cells are generated through knockdown of the HPRT gene. In some embodiments, an amount of MTX administered ranges from about 2 mg/m$^2$/infusion to about 8 mg/m$^2$/infusion. In some embodiments, an amount of MTX administered ranges from about 2.5 mg/m$^2$/infusion to about 7.5 mg/m$^2$/infusion.

In another aspect of the present disclosure is a method of treating cancer in a patient in need of treatment thereof comprising: generating tumor-antigen-specific T-cells which are HPRT deficient; positively selecting for the HPRT deficient tumor-antigen-specific T-cells ex vivo to provide a population of tumor-antigen-specific T-cells for administration; administering the population of modified tumor-antigen-specific T-cells to the patient; and optionally administering at least one dose of MTX to suppress at least one symptom of GVHD.

In another aspect of the present disclosure is a method of providing benefits of a lymphocyte infusion while mitigating side effects in a patient comprising (i) administering modified T-cells that are HPRT-deficient to the patient (such as following an HSC graft); and (ii) administering MTX to the patient upon an onset of side effects. In some embodiments, the side effects are selected from the group consisting of aGVHD or cGVHD. In some embodiments, the modified T-cells are administered in a single dose. In some embodiments, an amount of modified T-cells administered in the single dose ranges from about $0.1 \times 10^6$/kg body weight to about $730 \times 10^6$/kg body weight. In some embodiments, the modified T-cells are administered over multiple doses. In some embodiments, an amount of modified T-cells administered per dose ranges from about $0.1 \times 10^6$/kg body weight to about $240 \times 10^6$/kg body weight. In some embodiments, the MTX is administered as a single dose. In some embodiments, multiple doses of the MTX are administered. In some embodiments, an amount of MTX administered ranges from about 2 mg/m$^2$/infusion to about 8 mg/m$^2$/infusion. In some embodiments, the amount of MTX administered ranges from about 2.5 mg/m$^2$/infusion to about 7.5 mg/m$^2$/infusion.

In another aspect of the present disclosure is a method of inducing a graft-versus-malignancy effect in a patient following stem cell transplantation comprising (i) administering modified T-cells that are HPRT-deficient to the patient (such as following an HSC graft); and (ii) monitoring the patient for an onset of side effects. In some embodiments, the side effects are selected from the group consisting of aGVHD or cGVHD. In some embodiments, the method further comprises administering MTX to the patient upon onset of the side effects. In some embodiments, the modified T-cells are administered in a single dose. In some embodiments, an amount of modified T-cells administered in the single dose ranges from about $0.1 \times 10^6$/kg body weight to about $730 \times 10^6$/kg body weight. In some embodiments, the modified T-cells are administered over multiple doses. In some embodiments, an amount of modified T-cells administered per dose ranges from about 0.1×10⁶/kg body weight to about 240×10⁶/kg body weight. In some embodiments, the MTX is administered as a single dose. In some embodiments, multiple doses of the MTX are administered. In some embodiments, an amount of MTX administered ranges from about 2 mg/m²/infusion to about 8 mg/m²/infusion. In some embodiments, the amount of MTX administered ranges from about 2.5 mg/m²/infusion to about 7.5 mg/m²/infusion.

In another aspect of the present disclosure is a method of treating cancer comprising (i) administering a gene-modified adoptive immunotherapy that is HPRT-deficient to a subject in need thereof; (ii) monitoring the subject for an onset of side effects; and (iii) administering MTX upon onset of the side effects. In some embodiments, the gene-modified adoptive immunotherapy is selected from the group consisting of CAR-modified cells, autologous and allogenic CAR-modified cells, autologous TCR-modified cells, and allogenic TCR-modified cells.

In another aspect of the present disclosure is a method of treating cancer comprising (i) administering CAR T-cells that are HPRT-deficient to a subject in need thereof; and (ii) monitoring the subject for an onset of side effects. In some embodiments, the side effects are selected from the group consisting of aGVHD or cGVHD. In some embodiments, the method further comprises administering MTX upon onset of the side effects. In some embodiments, the modified T-cells are administered in a single dose. In some embodiments, an amount of modified T-cells administered in the single dose ranges from about 0.1×10⁶/kg body weight to about 730×10⁶/kg body weight. In some embodiments, the modified T-cells are administered over multiple doses. In some embodiments, an amount of modified T-cells administered per dose ranges from about 0.1×10⁶/kg body weight to about 240×10⁶/kg body weight. In some embodiments, the MTX is administered as a single dose. In some embodiments, multiple doses of the MTX are administered. In some embodiments, an amount of MTX administered ranges from about 2 mg/m²/infusion to about 8 mg/m²/infusion. In some embodiments, the amount of MTX administered ranges from about 2.5 mg/m²/infusion to about 7.5 mg/m²/infusion.

In another aspect of the present disclosure is a method of treating cancer comprising (i) administering TCR-modified T-cells that are HPRT-deficient to a subject in need thereof; and (ii) monitoring the subject for an onset of side effects. In some embodiments, the side effects are selected from the group consisting of aGVHD or cGVHD. In some embodiments, the method further comprises administering MTX upon onset of the side effects. In some embodiments, the modified T-cells are administered in a single dose. In some embodiments, an amount of modified T-cells administered in the single dose ranges from about 0.1×10⁶/kg body weight to about 730×10⁶/kg body weight. In some embodiments, the modified T-cells are administered over multiple doses. In some embodiments, an amount of modified T-cells administered per dose ranges from about 0.1×10⁶/kg body weight to about 240×10⁶/kg body weight. In some embodiments, the MTX is administered as a single dose. In some embodiments, multiple doses of the MTX are administered. In some embodiments, an amount of MTX administered ranges from about 2 mg/m²/infusion to about 8 mg/m²/infusion. In some embodiments, the amount of MTX administered ranges from about 2.5 mg/m²/infusion to about 7.5 mg/m²/infusion.

In another aspect of the present disclosure is a method of preserving a graft versus malignancy effect while mitigating graft versus host disease in a subject by administrating to the subject a therapeutically effective amount of modified T-cells and administering MTX upon onset of GVHD. In some embodiments, the graft versus malignancy effect is a graft versus leukemia effect.

In another aspect of the present disclosure is a method of treating a patient with cancer who has received an allogeneic hematopoietic cell transplant, comprising administering to the patient a therapeutically effective amount of modified T-cells (e.g. those that are HPRT deficient), the modified T-cells being HPRT-deficient; monitoring for an onset of side effects resulting from the administration of the modified T-cells; and administering MTX to suppress, reduce, or control the side effect while maintaining a graft-versus malignancy reaction effective to eliminate or reduce the number of cancer cells in the patient. In some embodiments, the method further comprises administering a therapeutically effective amount of a corticosteroid. In some embodiments, the "effective amount" is an amount of that reduces or eliminates one or more undesirable symptoms associated with graft-versus-host disease (GVHD) that arises as a consequence of DLI. In some embodiments, the modified T-cells are administered as a bolus transfusion. In other embodiments, multiple administrations of the modified T-cells are provided, i.e. multiple transfusions are administered. In some embodiments, the modified T-cells are produced according to the methods described herein, such as illustrated in FIG. 1. In some embodiments, a single dosage of MTX is administered. In other embodiments, the amount of MTX administered depends upon the severity of the onset of GVHD and, in that regard, the dose (or dosages) of MTX may be titrated to achieve a desired reduction in GVHD symptoms and/or a desired level of the GVM effect.

In another aspect of the present disclosure is a method of treating cancer comprising (i) administering to a patient having cancer a therapeutically effective amount of substantially purified modified T-cells, the modified T-cells being HPRT-deficient; and (ii) monitoring the patient for the presence of cancer and for the onset of GVHD. In some embodiments, a therapeutically effective amount of MTX is administered upon onset of GVHD.

Applicant have found that a gene-modified heterogeneous T-cell population can provide a more complete immunologic reconstitution for immunocompromised transplantation patients (e.g. those having severe Crohn's disease, irritable bowel syndrome, or aplastic anemia). In addition, because the antigen specificity of the GVM effector cells is not completely clear, the use of the entire T-cell repertoire is believed to be the best option for obtaining a GVM effect.

Moreover, in comparison to other "off switch" methods, cells treated according to the disclosed methods do not need to express a "suicide gene." (see, for example, Di Stasi A, Tey S K, Dotti G, Fujita Y, Kennedy-Nasser A, Martinez C, Straathof K, Liu E, Durett A G, Grilley B, Liu H, Cruz C R, Savoldo B, Gee A P, Schindler J, Krance R A, Heslop H E, Spencer D M, Rooney C M, Brenner M K. Inducible apoptosis as a safety switch for adoptive cell therapy. N Engl J Med. 2011 Nov. 3; 365(18):1673-83; Xu K, Zhu F, Du B, Gao F, Cheng H, Pan X. Prophylaxis of graft-versus-host disease by lentiviral-mediated expression of herpes simplex virus-thymidine kinase and ganciclovir treatment. Transplant Proc. 2008 October; 40(8):2665-9; and Philip B, Kokalaki E, Mekkaoui L, Thomas S, Straathof K, Flutter B, Marin V, Marafioti T, Chakraverty R, Linch D, Quezada S A, Peggs K S, Pule M. A highly compact epitope-based marker/suicide gene for easier and safer T-cell therapy. Blood. 2014 Aug. 21; 124(8):1277-87, the disclosures of which are each hereby incorporated by reference herein in their entireties). Rather, the disclosed method provides for knockdown or knockout of an endogenous gene that causes no undesirable effects in hematological cells and, overall, superior results. Applicant submit that due to ex vivo 6TG chemoselection of gene-modified cells, there exists a very high purity of engineered cells to permit the quantitative elimination of cells in vivo via MTX dosing. In addition, treatment according to the disclosed methods provides for potentially higher doses and a more aggressive therapy of donor T-cells than therapy where a "kill switch" is not incorporated. Further, the use of MTX to regulate the number of modified T-cells is clinically compatible with existing methods of treating GVHD, i.e. where MTX is used to help alleviate GVHD symptoms in patients not receiving the disclosed modified T-cells.

Finally, Applicant submits that in comparison to donor lymphocytes transduced with the herpes simplex thymidine kinase gene, treatment according to the disclosed methods mitigates limitations including immunogenicity resulting in the elimination of the cells and precluding the possibility of future infusions. (see Zhou X, Brenner M K. Improving the safety of T-Cell therapies using an inducible caspase-9 gene. Exp Hematol. 2016 November; 44(11):1013-1019, the disclosure of which is hereby incorporated by reference herein in its entirety). Also, the present methods allow for use of ganciclovir for concurrent clinical conditions other than GVHD without resulting in undesired clearance of HSV-tk donor lymphocytes (e.g. ganciclovir would not be precluded from being administered to control CMV infections, which are common in the allo-HSCT setting, when the currently described methods are utilized).

BRIEF DESCRIPTION OF THE FIGURES

FIGS. 10A and 10B illustrate the effect of positive selection with 6TG (ex vivo) on CEM cells.

FIGS. 12A and 12B illustrate the effect of negative selection with MTX on CEM cells.

SEQUENCE LISTING

Figure 1:
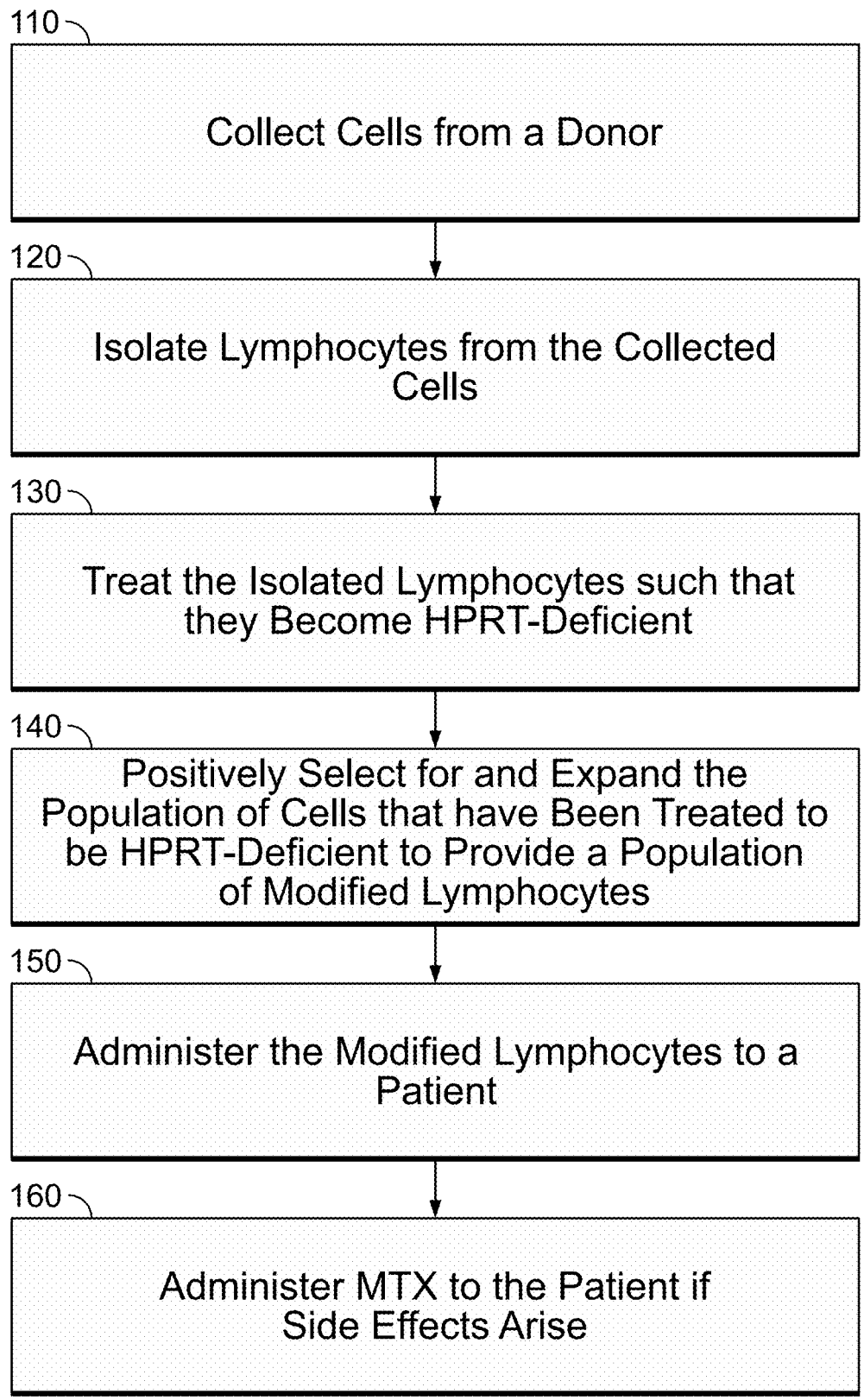
FIG. 1 is a flow chart illustrating the steps of preparing modified T-cells and administering those modified T-cells to a patient in need thereof.

The nucleic acid sequence provide herein is shown using standard letter abbreviations for nucleotide bases as defined in 37 C.F.R. 1.822. The sequence listing is submitted as an ASCII text file, named "2018-07-13_Calimmune-036WO_ST25.txt" created on Jul. 13, 2018, less than 1 KB, which is incorporated by reference herein.

DETAILED DESCRIPTION

The disclosed methods are generally directed to preventing, treating, suppressing, controlling or otherwise mitigating side effects of T-cell therapy, the T-cell therapy designed to accelerate immune reconstitution, induce a GVM effect, and/or target tumor cells.

Definitions

As used herein, the singular terms "a," "an," and "the" include plural referents unless the context clearly indicates otherwise. Similarly, the word "or" is intended to include "and" unless the context clearly indicates otherwise. Thus, for example, reference to "a cell" includes a plurality of such cells and a reference to "the protein" includes reference to one or more proteins and equivalents thereof known to those skilled in the art, and so forth. All technical and scientific terms used herein have the same meaning as commonly understood to one of ordinary skill in the art to which this disclosure belongs unless clearly indicated otherwise.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c.

Moreover, while the steps and processes may be outlined herein in a particular order, the skilled artisan will recognize that the ordering steps and processes may vary.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of" "Consisting essentially of," when used in the claims, shall have its ordinary meaning as used in the field of patent law.

As used herein, the term "administration" as it applies to a subject or patient, a placebo subject, a research subject, an experimental subject, a cell, a tissue, an organ, or a biological fluid, refers, without limitation, to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell.

"Allogeneic T-cell" refers to a T-cell from a donor having a tissue HLA type that matches the recipient. Typically, matching is performed based on variability at three or more loci of the HLA gene, and a perfect match at these loci is preferred. In some instances, allogeneic transplant donors may be related (usually a closely HLA matched sibling), syngeneic (a monozygotic 'identical' twin of the patient) or unrelated (donor who is not related and found to have very close degree of HLA matching). The HLA genes fall in two categories (Type I and Type II). In general, mismatches of the Type-I genes (i.e. HLA-A, HLA-B, or HLA-C) increase the risk of graft rejection. A mismatch of an HLA Type II gene (i.e. HLA-DR, or HLA-DQB1) increases the risk of graft-versus-host disease.

As used herein, the terms "CAR T" or "CAR-T cells" refer to a T-cell or population thereof, which has been modified through methods to express a chimeric antigen receptor (CAR) on the T-cell surface. The CAR is a polypeptide having a pre-defined binding specificity to a desired target expressed operably connected to (e.g., as a fusion, separate chains linked by one or more disulfide bonds, etc.) the intracellular part of a T-cell activation domain.

As used herein, the terms "effective amount" or "therapeutically effective amount" encompasses, without limitation, an amount that can ameliorate, suppress, control, reverse, mitigate, prevent, or diagnose a symptom or sign of a medical condition or disorder. Unless dictated otherwise, explicitly or by context, an "effective amount" is not limited to a minimal amount sufficient to ameliorate, suppress, control, or reverse a condition.

As used herein, the terms "hematopoietic cell transplant" or "hematopoietic cell transplantation" refer to bone marrow transplantation, peripheral blood stem cell transplantation, umbilical vein blood transplantation, or any other source of pluripotent hematopoietic stem cells. Likewise, the terms the terms "stem cell transplant," or "transplant," refer to a composition comprising stem cells that are in contact with (e.g. suspended in) a pharmaceutically acceptable carrier. Such compositions are capable of being administered to a subject through a catheter.

Figure 5:
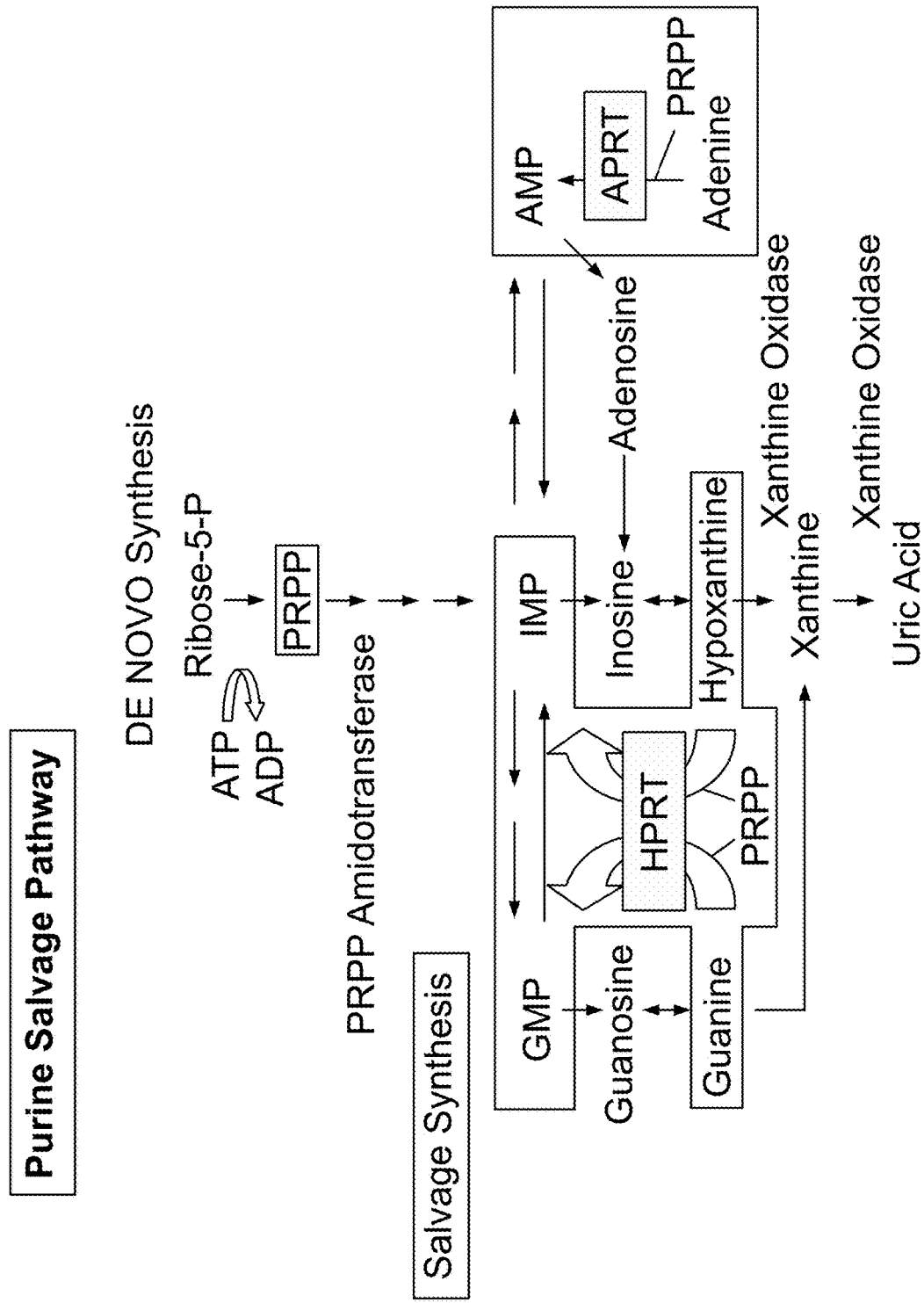
FIG. 5 illustrates the purine salvage pathway.

As used herein, "HPRT" is an enzyme involved in purine metabolism encoded by the HPRT1 gene. HPRT1 is located on the X chromosome, and thus is present in single copy in males. HPRT1 encodes the transferase that catalyzes the conversion of hypoxanthine to inosine monophosphate and guanine to guanosine monophosphate by transferring the 5-phosphorobosyl group from 5-phosphoribosyl 1-pyrophosphate to the purine. The enzyme functions primarily to salvage purines from degraded DNA for use in renewed purine synthesis (see FIG. 5).

As used herein, the terms "knock down" or "knockdown" when used in reference to an effect of RNAi on gene expression, means that the level of gene expression is inhibited, or is reduced to a level below that generally observed when examined under substantially the same conditions, but in the absence of RNAi.

As used herein, the terms "knock out" or "knockout" refer to partial or complete suppression of the expression of an endogenous gene. This is generally accomplished by deleting a portion of the gene or by replacing a portion with a second sequence, but may also be caused by other modifications to the gene such as the introduction of stop codons, the mutation of critical amino acids, the removal of an intron junction, etc. Accordingly, a "knockout" construct is a nucleic acid sequence, such as a DNA construct, which, when introduced into a cell, results in suppression (partial or complete) of expression of a polypeptide or protein encoded by endogenous DNA in the cell. In some embodiments, a "knockout" includes mutations such as, a point mutation, an insertion, a deletion, a frameshift, or a missense mutation As used herein, the term "lentiviral vector" is used to denote any form of a nucleic acid derived from a lentivirus and used to transfer genetic material into a cell via transduction. The term encompasses lentiviral vector nucleic acids, such as DNA and RNA, encapsulated forms of these nucleic acids, and viral particles in which the viral vector nucleic acids have been packaged.

As used herein, the terms "subject," or "patient," refers to a vertebrate animal, including a mammal. A human, *Homo sapiens*, is considered a subject or patient.

As used herein, the term "T cell receptor" or "TCR" refers to a complex of membrane proteins that participate in the activation of T-cells in response to the presentation of antigen. The TCR is believed to be responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T-cell, a memory T cell, regulatory T-cell, natural killer T-cell, and gamma delta T-cell.

As used herein, the terms "TCR-modified T cell" or "modified TCTTCR T-cells" mean T-cells that comprise altered specificity or which lack expression of a functional TCR. In some embodiments, the TCR-modified T-cells are modified such that they possess enhanced tumor-killing activity, i.e. they are modified such that they efficiently recognize antigen-bearing tumor cells.

As used herein, the term "titration" refers to the continual adjustment of a dose based on patient response. For example, dosages may be adjusted until a desired clinical effect is observed or achieved.

As used herein, the terms "transduce" or "transduction" refers to the delivery of a gene(s) using a viral or retroviral vector by means of infection rather than by transfection. For example, an anti-HIV gene carried by a retroviral vector (a modified retrovirus used as a vector for introduction of nucleic acid into cells) can be transduced into a cell through infection and provirus integration. Thus, a "transduced gene" is a gene that has been introduced into the cell via lentiviral or vector infection and provirus integration. Viral vectors (e.g., "transducing vectors") transduce genes into "target cells" or host cells.

As used herein, the terms "treatment," "treating," or "treat," with respect to a specific condition, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease and/or relieving one or more disease symptoms. "Treatment" can also encompass delivery of an agent or administration of a therapy in order to provide for a pharmacologic effect, even in the absence of a disease or condition. The term "treatment" is used in some embodiments to refer to administration of a compound of the present disclosure to mitigate a disease or a disorder in a host, preferably in a mammalian subject, more preferably in humans. Thus, the term "treatment" can include includes: preventing a disorder from occurring in a host, particularly when the host is predisposed to acquiring the disease but has not yet been diagnosed with the disease; inhibiting the disorder; and/or alleviating or reversing the disorder. Insofar as the methods of the present disclosure are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present disclosure can occur prior to onset of a disease. The term does not mean that the disease state must be completely avoided.

As used herein, the term "vector" refers to a nucleic acid molecule capable of mediating entry of, e.g., transferring, transporting, etc., another nucleic acid molecule into a cell. The transferred nucleic acid is generally linked to, e.g., inserted into, the vector nucleic acid molecule. A vector may include sequences that direct autonomous replication or may include sequences sufficient to allow integration into host cell DNA. As will be evident to one of ordinary skill in the art, viral vectors may include various viral components in addition to nucleic acid(s) that mediate entry of the transferred nucleic acid. Numerous vectors are known in the art including, but not limited to, linear polynucleotides, polynucleotides associated with ionic or amphiphilic compounds, plasmids, and viral vectors. Examples of viral vectors include, but are not limited to, adenoviral vectors, adeno-associated virus vectors, retroviral vectors (including lentiviral vectors), and the like.

Preparation of HPRT-Deficient T-Cells ("Modified T-Cells") In one aspect of the present disclosure is a method of producing HPRT-deficient T-cells (also referred to herein as "modified T-cells"). With reference to FIG. 1, cells, namely lymphocytes (T-cells), are first collected from a donor (step 110). In embodiments where hematopoietic stem cells (HSC) are also collected from a donor, the T-cells may be collected from the same donor from which the HSC graft is collected or from a different donor. In these embodiments, the cells may be collected at the same time or at a different time as the cells for the HSC graft. In some embodiments, the cells are collected from the same mobilized peripheral blood HSC harvest. In some embodiments, this could be a CD34-negative fraction (CD34-positive cells collected as per standard of care for donor graft), or a portion of the CD34-positive HSC graft if a progenitor T-cell graft is envisaged.

The skilled artisan will appreciate that the cells may be collected by any means. For example, the cells may be collected by apheresis, leukapheresis, or merely through a simple venous blood draw. In embodiments where the HSC graft is collected contemporaneously with the cells for modification, the HSC graft is cryopreserved so as to allow time for manipulation and testing of the T-cells collected.

Following collection of the cells, T-cells are isolated (step 120). The T-cells may be isolated from the aggregate of cells collected by any means known to those of ordinary skill in the art. For example, CD3+ cells may be isolated from the collected cells via CD3 microbeads and the MACS separation system (Miltenyi Biotec). It is believed that the CD3 marker is expressed on all T-cells and is associated with the T-cell receptor. It is believed that about 70 to about 80% of human peripheral blood lymphocytes and about 65-85% of thymocytes are CD3+. In some embodiments, the CD3+ cells are magnetically labeled with CD3 MicroBeads. Then the cell suspension is loaded onto a MACS Column which is placed in the magnetic field of a MACS Separator. The magnetically labeled CD3+ cells are retained on the column. The unlabeled cells run through and this cell fraction is depleted of CD3+ cells. After removal of the column from the magnetic field, the magnetically retained CD3+ cells can be eluted as the positively selected cell fraction.

Alternatively, CD62L+ T-cells may be isolated from the collected cells is via an IBA life sciences CD62L Fab Streptamer Isolation Kit. Isolation of human CD62L+ T-cells is performed by positive selection. PBMCs are labeled with magnetic CD62L Fab Streptamers. Labeled cells are isolated in a strong magnet where they migrate toward the tube wall on the side of the magnet. This CD62L positive cell fraction is collected and cells are liberated from all labeling reagents by addition of biotin in a strong magnet. The magnetic Streptamers migrate toward the tube wall and the label-free cells remain in the supernatant. Biotin is removed by washing. The resulting cell preparation is highly enriched with CD62L+ T-cells with a purity of more than 90%. No depletion steps and no columns are needed.

In alternative embodiments, T-cells are not isolated at step 120, but rather the aggregate of cells collected at step 110 are used for subsequent modification. While in some embodiments the aggregate of cells may be used for subsequent modification, in some instances the method of modification may be specific for a particular cell population within the total aggregate of cells. This could be done in a number of ways; for example, targeting genetic modification to a particular cell type by targeting gene vector delivery, or by targeting expression of, for example a shRNA to HPRT to a particular cell type, i.e., T-cells.

Following isolation of the T-cells, the T-cells are treated to decrease HPRT activity (step 130), i.e. to crease expression of the HPRT gene. The T-cells may be modified according to several methods. In some embodiments, the T-cells may be modified utilizing an RNA interference technique. RNA interference (RNAi) has recently become an important genetic approach for post-transcriptional silencing of gene expression by triggering degradation of homologous transcripts through a complex multistep enzymatic process involving sequence-specific double-stranded small interfering RNA (siRNA). In some embodiments, T-cells may be modified by transduction with a vector, e.g. a lentiviral vector, encoding a shRNA targeted to the HPRT gene. In some embodiments the shRNA may be embedded within a miRNA framework (amiRNA), in other embodiments the shRNA may be of the Dicer-independent Ago-shRNA design. Here, the precursor shRNA constructs are intracellularly processed to generate siRNA duplexes. Lentiviral vectors have emerged as potent and versatile tools for this purpose as they offer the ability to efficiently infect a wide variety of primary cell types, whether dividing or non-dividing, and can achieve stable vector integration into the target cell genome, thereby enabling long-term modification of the cellular phenotype. In some embodiments, the lentiviral vector is a self-inactivating lentiviral vector. Methods of preparing a suitable lentiviral vector are described by Hacke K, et al., Genetic modification of mouse bone marrow by lentiviral vector-mediated delivery of hypoxanthine-Guanine phosphoribosyltransferase short hairpin RNA confers chemoprotection against 6-thioguanine cytotoxicity, Transplant Proc. 2013 June; 45(5):2040-4, the disclosure of which is incorporated by reference herein in its entirety. In alternative embodiments, T-cells may be modified by transduction with non-integrating lentiviral vectors or other viral vectors (AAV vectors).

In some embodiments, the shRNA has a sequence having at least 80% identify to that of SEQ ID NO: 1. In other embodiments, the shRNA has a sequence having at least 90% identify to that of SEQ ID NO:1. In yet other embodiments, the shRNA has a sequence having at least 95% identity to that of SEQ ID NO: 1. In further embodiments, the shRNA has a sequence having at least 97% identity to that of SEQ ID NO: 1. In even further embodiments, the shRNA has a sequence having at least 98% identity to that of SEQ ID NO: 1. In yet further embodiments, the shRNA has a sequence having at least 99% identity to that of SEQ ID NO: 1. Other suitable shRNA molecules are described in PCT Publication No. WO/2017/143266, the disclosure of which is hereby incorporated by reference herein in its entirety.

In other embodiments, a gene editing approach may be used to knockout HPRT. For example, isolated cells may be treated with a HPRT-targeted CRISPR/Cas9 RNP. In some embodiments, the HPRT-targeted CRISP/Cas9 RNP may be formulated within a nanocapsule. Maeder M L et al. Genome-editing Technologies for Gene and Cell Therapy, Mol Ther. 2016 March; 24(3):430-46), describe various gene editing techniques, including CRISPR/Cas9 nuclease mediated methods, and these disclosures are hereby incorporated by reference herein in their entirety. Gene editing tools may also be delivered via any method known to those of ordinary skill in the art including by way of AAV vectors, non-integrating and non-reverse transcribed lentiviral vectors, and other physical delivery methods (e.g. electroporation, cell squeezing, sonoporation, etc.). Transfection methods including calcium phosphate, lipofectamine, fugene, dendrimers, liposomes (usually cationic liposomes), and other cationic polymers (e.g., DEAE or PEI) may also be utilized. There also other exist other particle-based methods including nanoparticle delivery systems, which may be biologically or chemically functionalized to increase delivery, or may be used in physical methods of delivery, e.g., magnofection, or particle bombardment.

In some embodiments, electroporation is used to introduce nucleic acids into eukaryotic cells, such as by opening transient pores in the cell member to allow the uptake of material. Electroporation is a method whereby DNA (or RNA) is introduced into cells by passing an electric current across the cell membrane.

Other gene editing techniques using certain nucleases are described in U.S. Pat. Nos. 8,895,264 and 9,22,105, the disclosures of which are hereby incorporated by reference herein in their entireties. In some embodiments, a zinc-finger protein (ZFP) that binds to a target site in an HPRT gene in a genome may be utilized, wherein the ZFP comprises one or more engineered zinc-finger binding domains. In some embodiments, ZFPs are used as a pair of zinc-finger nucleases (ZFNs) that dimerize and then cleave a target genomic region of interest, wherein the ZFNs comprise one or more engineered zinc-finger binding domains and a nuclease cleavage domain or cleavage half-domain. In some embodiments, a TALE protein (Transcription activator like effector) that binds to target site in an HPRT gene in a genome may be utilized, wherein the TALE comprises one or more engineered TALE DNA binding domains. In some embodiments, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains of ZFNs and/or TALENs can be obtained, for example, from various restriction endonucleases and/or homing endonucleases. In some embodiments, the cleavage half-domains are derived from a Type IIS restriction endonuclease (e.g., Fok I).

After the T-cells are modified at step 130, the population of HPRT-deficient T-cells is selected for and/or expanded (step 140). In some embodiments, the culture may concurrently select for and expand cells with enhanced capacity for engraftment (e.g. central memory or T stem cell phenotype). In some embodiments, the culture period is less than 14 days. In some embodiments, the culture period is less than 7 days.

Figure 6:
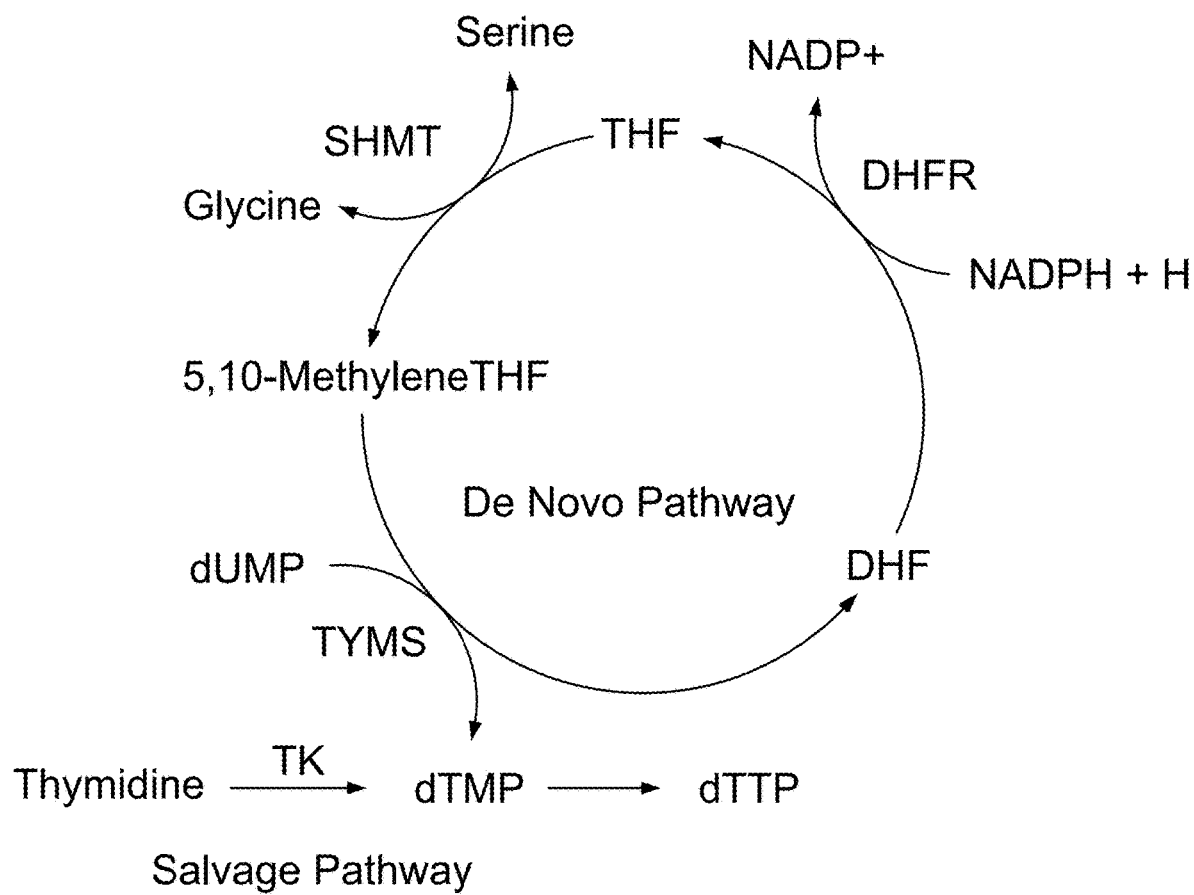
FIG. 6 illustrates the de novo path for the synthesis of dTTP.
Figure 7:
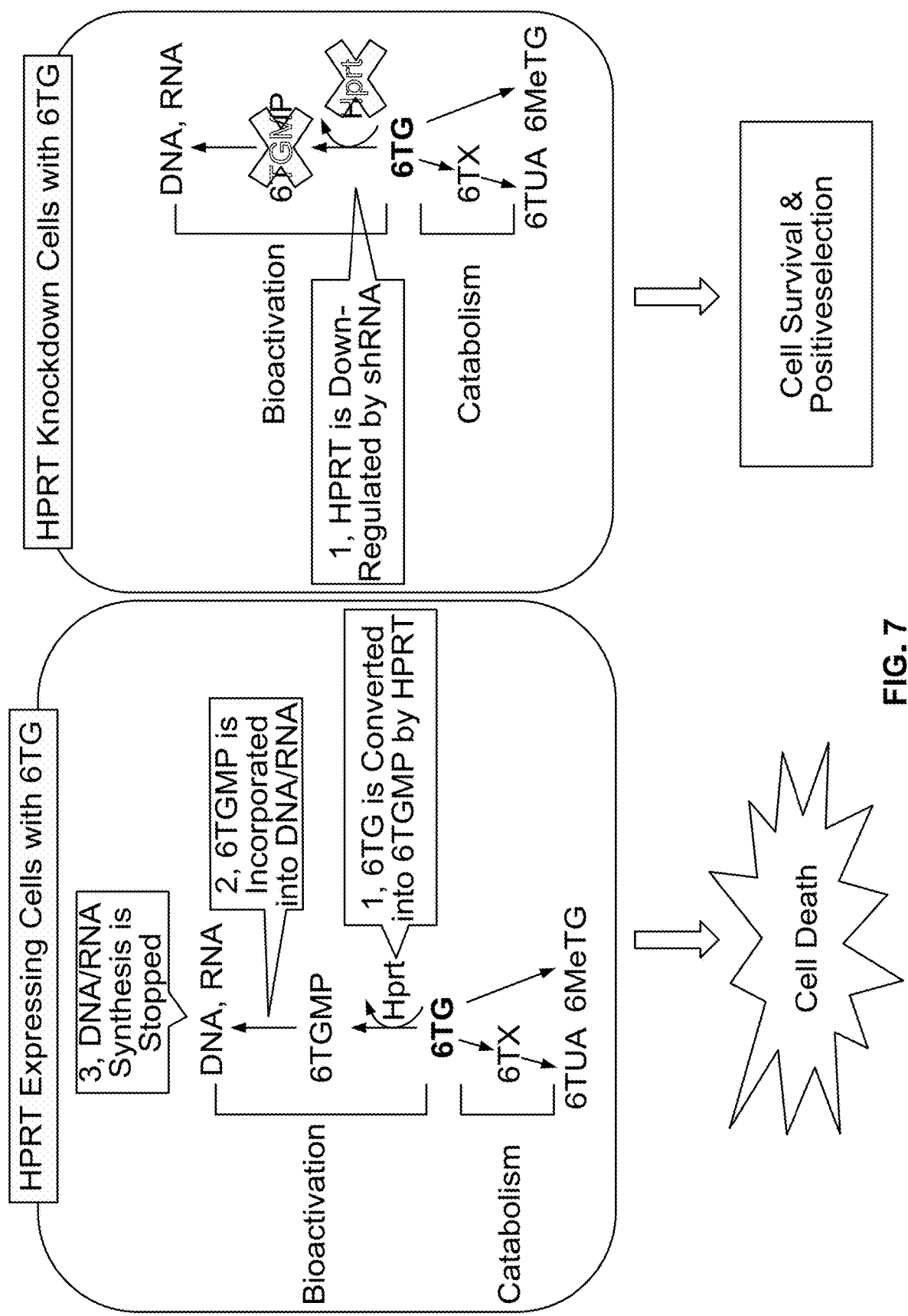
FIG. 7 illustrates the selection of HPRT-deficient cells in the presence of 6TG.
Figure 8:
FIG. 8 illustrates sh734 (SEQ ID NO: 1) driven by a 7sk promoter.

In some embodiments, the step of selecting for and expanding cells comprises treating the population of HPRT-deficient T-cells ex vivo with a guanosine analog antimetabolite (such as 6-thioguanine (6TG), 6-mercaptopurine (6-MP), or azathiopurine (AZA). In some embodiments, the T-cells are cultured in the presence of 6-thioguanine ("6TG"), thus killing cells which have not been modified at step 130. 6TG is a guanine analog that can interfere with dGTP biosynthesis in the cell. Thio-dG can be incorporated into DNA during replication in place of guanine, and when incorporated, often becomes methylated. This methylation can interfere with proper mis-match DNA repair and can result in cell cycle arrest, and/or initiate apoptosis. 6TG has been used clinically to treat patients with certain types of malignancies due to its toxicity to rapidly dividing cells. In the presence of 6TG, HPRT is the enzyme responsible for the integration of 6TG into DNA and RNA in the cell, resulting in blockage of proper polynucleotide synthesis and metabolism (see FIG. 7). On the other hand, the salvage pathway is blocked in HPRT-deficient cells (see FIG. 7). Cells thus use the de novo pathway for purine synthesis (see FIG. 6). However, in HPRT wild type cells, cells use the salvage pathway and 6TG is converted to 6TGMP in the presence of HPRT. 6TGMP is converted by phosphorylation to thioguanine diphosphate (TGDP) and thioguanine triphosphate (TGTP). Simultaneously deoxyribosyl analogs are formed, via the enzyme ribonucleotide reductase. Given that 6TG is highly cytotoxic, it can be used as a selection agent to kill cells with a functional HPRT enzyme.

The generated HPRT-deficient cells are then contacted with a purine analog ex vivo. For the knockdown approach, it is believed that there still may be residual HPRT in the cells and that HPRT-knockdown cells can tolerate a range of purine analog, but will be killed at high dosages/amounts. In this situation, the concentration of purine analogs used for ex vivo selection ranges from about 10 nM to about 5 µM. In some embodiments, the concentration ranges from about 100 nM to about 2.5 µM. In other embodiments, the concentration ranges from about 200 nM to about 2 µM. In yet other embodiments, the concentration ranges from about 200 nM to about 1 µM.

For the knockout approach, HPRT it is believed that HPRT may be totally eliminated or near totally eliminated from HPRT-knockout cells and the generated HPRT-deficient cells will be highly tolerant to purine analogs. The centration of purine analogs used for ex vivo selection in this case ranges from about 10 nM to about 100 µM. In some embodiments, the concentration ranges from about 10 nM to about 80 µM. In other embodiments, the concentration ranges from about 10 nM to about 60 µM. In yet other embodiments, the concentration ranges from about 20 nM to about 40 µM.

In other embodiments, modification of the cells (e.g. through knockdown or knockout of HPRT) may be efficient enough such that ex vivo selection for the HPRT-deficient cells is not necessary, i.e. selection with 6TG or other like compound is not required.

Figure 14:
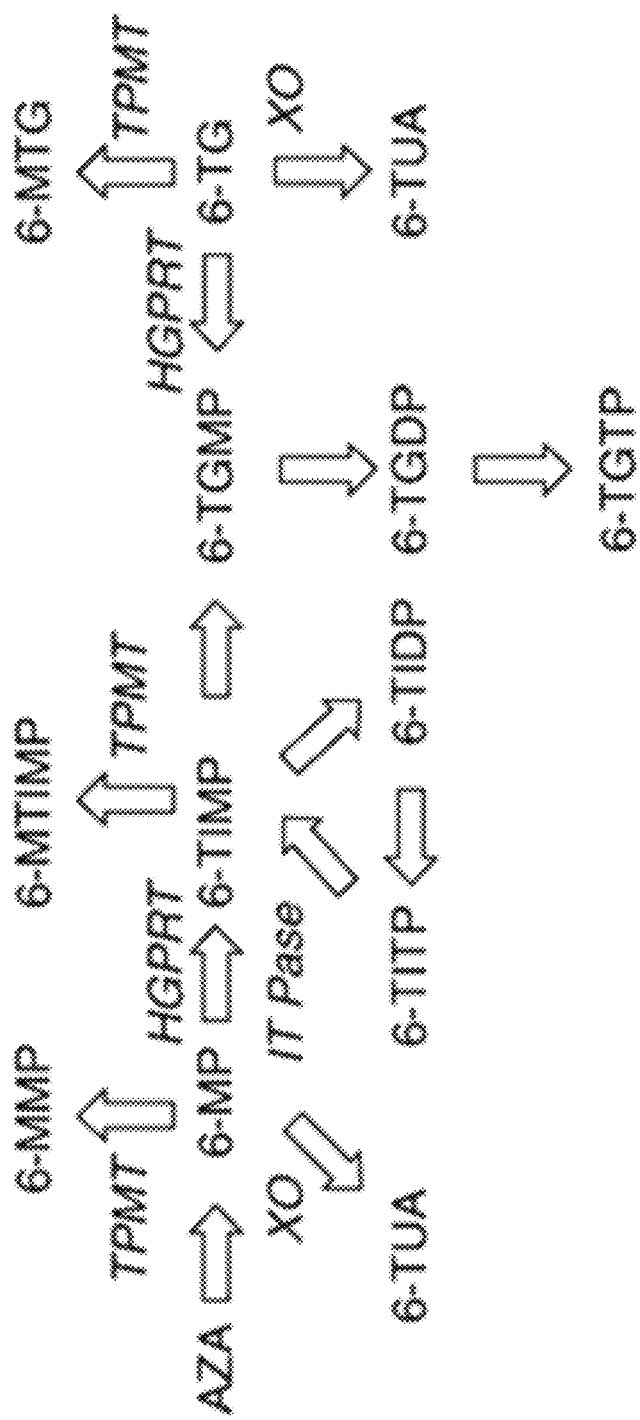
FIG. 14 illustrates the formation of toxic metabolites from 6TG.

In some embodiments, the generated HPRT-deficient cells are contacted with both a purine analog and with allopurinol, which is an inhibitor of xanthine oxidase (XO). By inhibiting XO, more available 6TG to be metabolized by HPRT. When 6TG is metabolized by HPRT it forms 6TGNs which are the toxic metabolites to the cells (6TGN encompasses 6-TG monophosphate (6TGMP), diphosphate (6-TGDP) and triphosphate (6TGTP)). (see FIG. 14). (see, for example, Curkovic et. al., Low allopurinol doses are sufficient to optimize azathioprine therapy in inflammatory bowel disease patients with inadequate thiopurine metabolite concentrations. Eur J Clin Pharmacol. 2013 August; 69(8):1521-31; Gardiner et. al. Allopurinol might improve response to azathioprine and 6-mercaptopurine by correcting an unfavorable metabolite ratio. J Gastroenterol Hepatol. 2011 January; 26(1):49-54; Seinen et. al. The effect of allopurinol and low-dose thiopurine combination therapy on the activity of three pivotal thiopurine metabolizing enzymes: results from a prospective pharmacological study. J Crohns Colitis. 2013 November; 7(10):812-9; and Wall et. al. Addition of Allopurinol for Altering Thiopurine Metabolism to Optimize Therapy in Patients with Inflammatory Bowel Disease. Pharmacotherapy. 2018 February; 38(2):259-270, the disclosures of each are hereby incorporated by reference herein in their entireties).

In some embodiments, allopurinol is introduced to the generated HPRT-deficient cells prior to introduction of the purine along. In other embodiments, allopurinol is introduced to the generated HPRT-deficient cells simultaneously with the introduction of the purine along. In yet other embodiments, allopurinol is introduced to the generated HPRT-deficient cells following the introduction of the purine along.

Following selection and expansion, the modified T-cell product is tested. In some embodiments, the modified T-cell product is tested according to standard release testing (e.g. activity, mycoplasma, viability, stability, phenotype, etc.; see Molecular Therapy: Methods & Clinical Development Vol. 4 Mar. 2017 92-101, the disclosure of which is hereby incorporated by reference herein in its entirety).

In other embodiments, the modified T-cell product is tested for sensitivity to MTX or mycophenolic acid (MPA). Both MTX and MPA inhibit de novo synthesis of purines but have different mechanisms of action. It is believed that MTX competitively inhibits dihydrofolate reductase (DHFR), an enzyme that participates in tetrahydrofolate (THF) synthesis. DHFR catalyzes the conversion of dihydrofolate to active tetrahydrofolate. Folic acid is needed for the de novo synthesis of the nucleoside thymidine, required for DNA synthesis. Also, folate is essential for purine and pyrimidine base biosynthesis, so synthesis will be inhibited. Mycophenolic acid (MPA) is potent, reversible, non-competitive inhibitor of inosine-5'-monophosphate dehydrogenase (IMPDH), an enzyme essential to the de novo synthesis of guanosine-5'-monophosphate(GMP) from inosine-5'-monophosphate (IMP).

MTX or MPA, therefore inhibits the synthesis of DNA, RNA, thymidylates, and proteins. MTX or MPA blocks the de novo pathway by inhibiting DHFR. In HPRT−/− cell, there is no salvage or de novo pathway functional, leading to no purine synthesis, and therefore the cells die. However, the HPRT wild type cells have a functional salvage pathway, their purine synthesis takes place and the cells survive. In some embodiments, the modified T-cells are HPRT-deficient. In some embodiments, at least 85% of the modified T-cells population is sensitive to MTX or MPA. In other embodiments, at least 90% of the modified T-cells population is sensitive to MTX or MPA. In yet other embodiments, at least 95% of the modified T-cells population is sensitive to MTX or MPA.

Given the sensitivity of the modified T-cells produced according to steps 110 through 140 to MTX or MPA, MTX or MPA may be used to selectively eliminate HPRT-deficient cells, as described herein.

Treatment with Modified T-Cells

In some embodiments, the modified T-cells prepared according to steps 110 to 140 are administered to a patient (step 150). In some embodiments, the modified T-cells (or CAR T-cells or TCR T-cells as described herein) are provided to the patient in a single administration (e.g. a single bolus, or administration over a set time period, for example and infusion over about 1 to 4 hours or more). In other embodiments, multiple administrations of the modified T-cells are made. If multiple doses of the modified T-cells are administered, each dose may be the same or different (e.g. escalating doses, decreasing doses).

In some embodiments, an amount of the dose of modified T-cells is determined based on the CD3-positive T-cell content/kg of the subject's body weight. In some embodiments, the total dose of modified T-cells ranges from about $0.1 \times 10^6$/kg body weight to about $730 \times 10^6$/kg body weight. In other embodiments, the total dose of modified T-cells ranges from about $1 \times 10^6$/kg body weight to about $500 \times 10^6$/kg body weight. In yet other embodiments, the total dose of modified T-cells ranges from about $1 \times 10^6$/kg body weight to about $400 \times 10^6$/kg body weight. In further embodiments, the total dose of modified T-cells ranges from about $1\times10^6$/kg body weight to about $300\times10^6$/kg body weight. In yet further embodiments, the total dose of modified T-cells ranges from about $1\times10^6$/kg body weight to about $200\times10^6$/kg body weight.

Where multiple doses are provided, the frequency of dosing may range from about 1 week to about 36 weeks. Likewise, where multiple doses are provided, each dose of modified T-cells ranges from about $0.1\times10^6$/kg body weight to about $240\times10^6$/kg body weight. In other embodiments, each dose of modified T-cells ranges from about $0.1\times10^6$/kg body weight to about $180\times10^6$/kg body weight. In other embodiments, each dose of modified T-cells ranges from about $0.1\times10^6$/kg body weight to about $140\times10^6$/kg body weight. In other embodiments, each dose of modified T-cells ranges from about $0.1\times10^6$/kg body weight to about $100\times10^6$/kg body weight. In other embodiments, each dose of modified T-cells ranges from about $0.1\times10^6$/kg body weight to about $60\times10^6$/kg body weight. Other dosing strategies are described by Gozdzik J et al., Adoptive therapy with donor lymphocyte infusion after allogenic hematopoietic SCT in pediatric patients, Bone Marrow Transplant, 2015 January; 50(1):51-5), the disclosure of which is hereby incorporated by reference in its entirety.

The modified T-cells may be administered alone or as part of an overall treatment strategy. In some embodiments, the modified T-cells are administered following an HSC transplant, such as about 2 to about 4 weeks after the HSC transplant. For example, in some embodiments, the modified T-cells are administered after administration of a HSC transplant to help prevent or mitigate post-transplant immune deficiency. It is believed that the modified T-cells may provide a short term (e.g. about 3 to about 9 month) immune reconstitution and/or protection. As another example, and in other embodiments, the modified T-cells are administrated as part of cancer therapy to help induce a graft-versus-malignancy (GVM) effect or a graft-versus-tumor (GVT) effect. As a further example, the modified T-cells are CAR-T cells or TCR-modified T-cells which are HPRT-deficient, and which are administered as part of a cancer treatment strategy. Administration of the modified T-cells according to each of these treatment avenues are described in more detail herein. Of course, the skilled artisan will appreciate that other treatments for any underlying condition may occur prior to, subsequent to, or concurrently with administration of the modified T-cells.

Suppression, Control, or Mitigation of Side Effects of T-cell Therapy

Administration of T-cells to a patient may result in unwanted side effects, including those recited herein. For example, graft-versus-host disease may occur after a patient is treated with T-cells, including modified T-cells (e.g. via knockdown or knockout of HPRT). In some aspects of the present disclosure, following administration of the modified T-cells at step 150, the patient is monitored for the onset of any side effects, including, but not limited to, GVHD. Should any side effects arise, such as GVHD (or symptoms of GVHD), MTX or MPA is administered to the patient (in vivo) at step 160 to remove at least a portion of the modified T-cells in an effort to suppress, reduce, control, or otherwise mitigate side effects, e.g. GVHD. In some embodiments, MTX or MPA is administered in a single dose. In other embodiments, multiple does of MTX and/or MPA are administered.

It is believed that the modified T-cells of the present disclosure (once selected for ex vivo and administered to the patient or mammalian subject), may serve as a modulatable "on"/"off" switch given their sensitivity to MTX (or MPA). The modulatable switch allows for regulation of immune system reconstitution by selectively killing at least a portion of the modified T-cells in vivo through the administration of MTX to the patient should any side effects occur. This modulatable switch may be further regulated by administering further modified T-cells to the patient following MTX administration to allow further immune system reconstitution after side effects have been reduced or otherwise mitigated. Likewise, the modulatable switch allows for regulation of a graft-versus-malignancy effect by selectively killing at least a portion of the modified T-cells in vivo through the administration of MTX should any side effects occur. Again, the GVM effect may be fine-tuned by subsequently dosing further aliquots of modified T-cells to the patient once side effects are reduced or otherwise mitigated. This same principle applies to CAR-T cell therapy or therapy with TCR-modified T-cells, where again the CAR-T cells or TCR-modified T-cells may be selectively turned on/off through MTX administration. In view of this, the person of ordinary skill in the art will appreciate that any medical professional overseeing treatment of a patient can balance immune system reconstitution and/or the GVM effect while keeping side effects at bay or within tolerable or acceptable ranges. By virtue of the above, patient treatment may be enhanced while mitigating adverse effects.

In some embodiments, an amount of MTX administered ranges from about 2 mg/m$^2$/infusion to about 100 mg/m$^2$/infusion. In some embodiments, an amount of MTX administered ranges from about 2 mg/m$^2$/infusion to about 90 mg/m$^2$/infusion. In some embodiments, an amount of MTX administered ranges from about 2 mg/m$^2$/infusion to about 80 mg/m$^2$/infusion. In some embodiments, an amount of MTX administered ranges from about 2 mg/m$^2$/infusion to about 70 mg/m$^2$/infusion. In some embodiments, an amount of MTX administered ranges from about 2 mg/m$^2$/infusion to about 60 mg/m$^2$/infusion. In some embodiments, an amount of MTX administered ranges from about 2 mg/m$^2$/infusion to about 50 mg/m$^2$/infusion. In some embodiments, an amount of MTX administered ranges from about 2 mg/m$^2$/infusion to about 40 mg/m$^2$/infusion. In some embodiments, an amount of MTX administered ranges from about 2 mg/m$^2$/infusion to about 30 mg/m$^2$/infusion. In some embodiments, an amount of MTX administered ranges from about 20 mg/m$^2$/infusion to about 20 mg/m$^2$/infusion. In some embodiments, an amount of MTX administered ranges from about 2 mg/m$^2$/infusion to about 10 mg/m$^2$/infusion. In some embodiments, an amount of MTX administered ranges from about 2 mg/m$^2$/infusion to about 8 mg/m$^2$/infusion. In other embodiments, an amount of MTX administered ranges from about 2.5 mg/m$^2$/infusion to about 7.5 mg/m$^2$/infusion. In yet other embodiments, an amount of MTX administered is about 5 mg/m$^2$/infusion. In yet further embodiments, an amount of MTX administered is about 7.5 mg/m$^2$/infusion.

In some embodiments, between 2 and 6 infusions are made, and the infusions may each comprise the same dosage or different dosages (e.g. escalating dosages, decreasing dosages, etc.). In some embodiments, the administrations may be made on a weekly basis, or a bi-monthly basis.

In yet other embodiments, the amount of MTX administered is titrated such that uncontrolled side effects, e.g. GVHD, is resolved, while preserving at least some modified T-cells and their concomitant effects on reconstituting the immune system, targeting cancer, or inducing the GVM effect. In this regard, it is believed that at least some of the benefit of the modified T-cells may still be recognized while ameliorating side effects, e.g. GVHD. In some embodiments, additional modified T-cells are administered following treatment with MTX, i.e. following resolution, suppression, or control of the side effects, e.g. GVHD.

In some embodiments, the subject receives doses of MTX prior to administration of the modified T-cells, such as to control or prevent side effects after HSC transplantation. In some embodiments, existing treatment with MTX is halted prior to administration of the modified T-cells, and then resumed, at the same or different dosage (and using a same or different dosing schedule), upon onset of side effects following treatment with the modified T-cells. In this regard, the skilled artisan can administer MTX on an as-need basis and consistent with the standards of care known in the medical industry.

In some embodiments, an alternative agent may be used in place of either MTX or MPA, including, but not limited to ribavarin (IMPDH inhibitor); VX-497 (IMPDH inhibitor) (see Jain J, VX-497: a novel, selective IMPDH inhibitor and immunosuppressive agent, J Pharm Sci. 2001 May; 90(5): 625-37); lometrexol (DDATHF, LY249543) (GAR and/or AICAR inhibitor); thiophene analog (LY254155) (GAR and/or AICAR inhibitor), furan analog (LY222306) (GAR and/or AICAR inhibitor) (see Habeck et al., A Novel Class of Monoglutamated Antifolates Exhibits Tight-binding Inhibition of Human Glycinamide Ribonucleotide Formyltransferase and Potent Activity against Solid Tumors, Cancer Research 54, 1021-2026, February 1994); DACTHF (GAR and/or AICAR inhibitor) (see Cheng et. al. Design, synthesis, and biological evaluation of 10-methanesulfonyl-DDACTHF, 10-methanesulfonyl-5-DACTHF, and 10-methylthio-DDACTHF as potent inhibitors of GAR Tfase and the de novo purine biosynthetic pathway; Bioorg Med Chem. 2005 May 16; 13(10):3577-85); AG2034 (GAR and/or AICAR inhibitor) (see Boritzki et. al. AG2034: a novel inhibitor of glycinamide ribonucleotide formyltransferase, Invest New Drugs. 1996; 14(3):295-303); LY309887 (GAR and/or AICAR inhibitor) ((2S)-2-[[5-[2-[(6R)-2-amino-4-oxo-5,6,7,8-tetrahydro-1H-pyrido[2,3-d]pyrimidin-6-yl]ethyl]thiophene-2-carbonyl]amino]pentanedioic acid); alimta (LY231514) (GAR and/or AICAR inhibitor) (see Shih et. al. LY231514, a pyrrolo[2,3-d]pyrimidine-based antifolate that inhibits multiple folate-requiring enzymes, Cancer Res. 1997 Mar. 15; 57(6):1116-23); dmAMT (GAR and/or AICAR inhibitor), AG2009 (GAR and/or AICAR inhibitor); forodesine (Immucillin H, BCX-1777; trade names Mundesine and Fodosine) (inhibitor of purine nucleoside phosphorylase [PNP]) (see Kicska et. al., Immucillin H, a powerful transition-state analog inhibitor of purine nucleoside phosphorylase, selectively inhibits human T lymphocytes, PNAS Apr. 10, 2001. 98 (8) 4593-4598); and immucillin-G (inhibitor of purine nucleoside phosphorylase [PNP]).

Prevention of Post-Transplant Immune Deficiency

Although hematopoietic stem cell transplantation from human leukocyte antigen (HLA) matched siblings has become a standard treatment modality for many hematological diseases (malignant and non-malignant), allogeneic HSC transplantation (allo-HSCT) remains the only proven curative therapy for chronic myeloid leukemia. The pluripotent hematopoietic stem cells required for this procedure are usually obtained from the bone marrow or peripheral blood of a related or unrelated donor. Historically, the best results of allogeneic HCT have been obtained when the stem cell donor is a HLA-matched sibling. However, any given sibling pair has only about a 25% chance of inheriting the same HLA haplotypes from their parents. This means that only about 30% of patients will have such a match. Consequently, attention has focused on other sources of stem cells. For patients who lack an HLA-matched sibling, alternative sources of donor grafts include suitably HLA-matched adult unrelated donors, umbilical cord blood stem cells, and partially HLA-mismatched, or HLA-haploidentical, related donors. The decision of which donor source to utilize depends, to a large degree, upon the clinical situation and the approaches employed at the individual transplant center. However, it is believed that almost all patients have at least one HLA-haploidentical mismatched family member (parent, child or sibling), who is immediately available as donor.

The major challenge of HLA-haploidentical HSCT is intense bi-directional alloreactivity leading to high incidences of graft rejection and GVHD. Advances in graft engineering and in pharmacologic prophylaxis of GVHD have reduced the risks of graft failure and GVHD after HLA-haploidentical HCT, and have made this stem cell source a viable alternative for patients lacking an HLA-matched sibling. However, it is believed that both of these approaches may lead to periods of post-transplant immunodeficiency rendering the recipient susceptible to infection, which is the primary cause of mortality not related to graft failure. It is believed that donor lymphocytes can play a central therapeutic role in the induction of immune reconstitution, especially in the subset of T-cell depleted matched transplants and in the context of partially mismatched transplants. Indeed, it is believed that DLI may be used after stem cell transplantation to prevent or mitigate infections and to establish full donor chimerism. The addition of mature T-cells which exhibit a broad repertoire of T-cell immunity against viral, fungal and other opportunistic infections might provide a clinical benefit (see, for example, Loren A W, Porter D L. Donor leukocyte infusions after unrelated donor hematopoietic stem cell transplantation. Curr Opin Oncol. 2006 March; 18(2):107-14; and Zhou X, et al. Long-term outcome after haploidentical stem cell transplant and infusion of T-cells expressing the inducible caspase 9 safety transgene. Blood. 2014 Jun. 19; 123(25):3895-905, the disclosures of which are hereby incorporated by reference herein, each in their entirety).

As noted herein, GVHD may occur after a patient is treated with a stem cell transplant. To combat this, the present disclosure provides a method of preventing or mitigating post-transplant immune deficiency and a pharmacological approach to reducing, suppressing or controlling GVHD should it arise. It is believed that the disclosed approach integrates with the practice of HLA-haploidentical HSCT described above. In some embodiments, the method utilizes an infusion of HPRT-deficient modified T-cells in patients post-allogenic HSCT to accelerate immune reconstitution and provide at least some immunity for the host while concomitantly being able to suppress or control GVHD via dosing with MTX.

Figure 2:
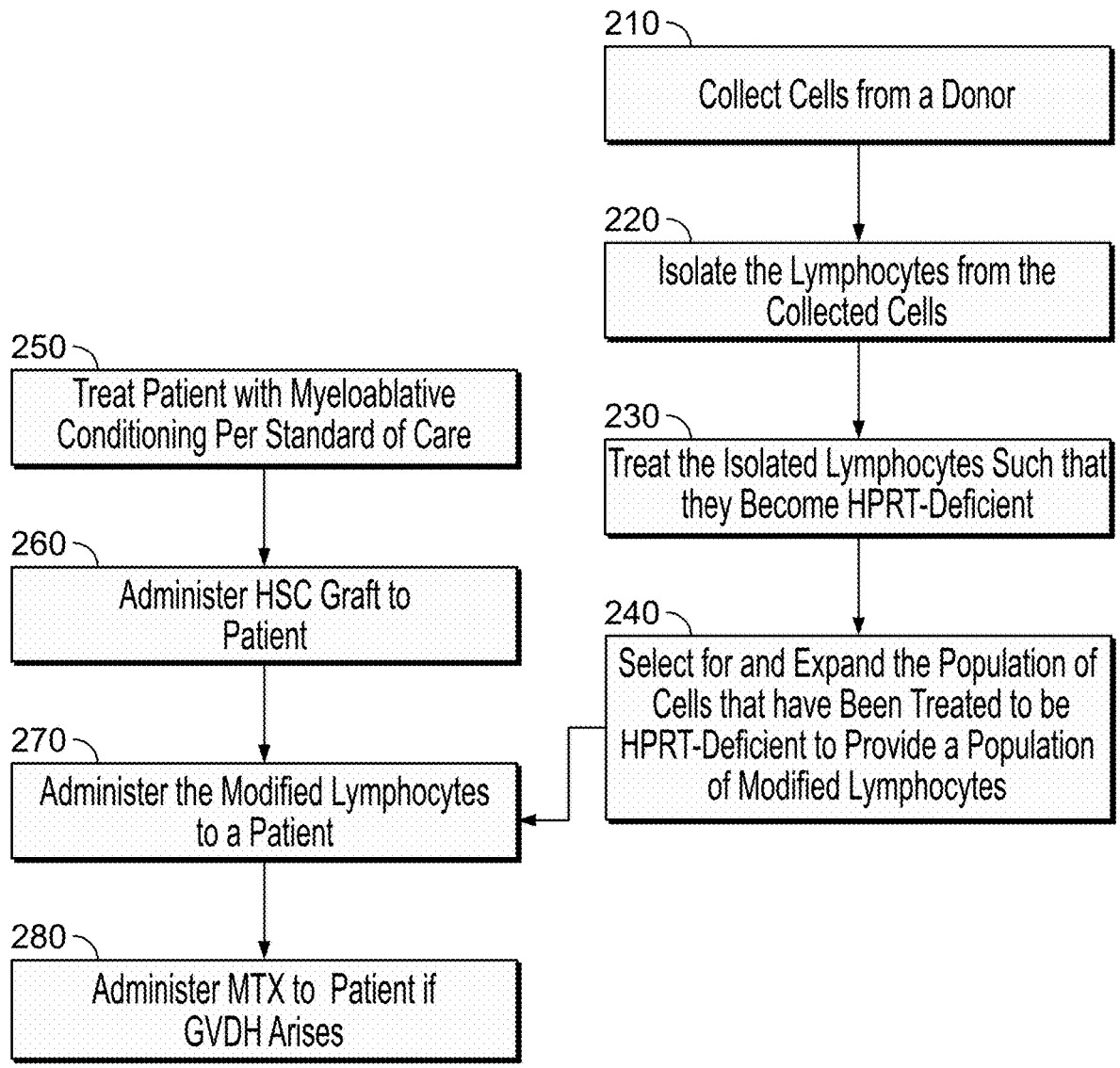
FIG. 2 is a flow chart illustrating the steps of preparing modified T-cells and administering those modified T-cells to a patient following a stem cell graft, such that the patient's immune system may be at least partially reconstituted.

FIG. 2 illustrates one method of reducing, suppressing, or controlling GVHD upon onset of symptoms. Initially, cells are collected from a donor at step 210. The cells may be collected from the same donor that provided the HSC for grafting (see step 260) or from a different donor. Lymphocytes are then isolated from the collected cells (step 220) and treated such that they become HPRT-deficient (step 230). Methods of treating the isolated cells are set forth herein. To arrive at a population of modified T-cells that are HPRT deficient, the treated cells are positively selected for and expanded (step 240), such as described herein. The modified T-cells are then stored for later use.

Prior to receiving the HSC graft (step 260), patients are treated with myeloablative conditioning as per the standard of care (step b 250) (e.g. high-dose conditioning radiation, chemotherapy, and/or treatment with a purine analog; or low-dose conditioning radiation, chemotherapy, and/or treatment with a purine analog).

In some embodiments, the patient is treated with the HSC graft (step 260) between about 24 and about 96 hours following treatment with the conditioning regimen. In other embodiments, the patient is treated with the HSC graft between about 24 and about 72 hours following treatment with the conditioning regimen. In yet other embodiments, the patient is treated with the HSC graft between about 24 and about 48 hours following treatment with the conditioning regimen. In some embodiments, the HSC graft comprises a minimum of $2\times10^6$ CD34+ cells/kg, with a target of greater than $6\times10^6$ CD34+ cells/kg.

Following HSC grafting, the modified T-cells from step 240 are administered to the patient according to standard transfusion protocols (step 270). In some embodiments, the modified T-cells are administered between about 2 to about 8 weeks after the HSC graft. In other embodiments, the modified T-cells are administered between about 2 to about 6 weeks after the HSC graft. In yet other embodiments, the modified T-cells are administered between about 2 to about 4 weeks after the HSC graft. In some embodiments, the modified T-cells are administered between about 1 day and about 21 days after the HSC graft. In some embodiments, the modified T-cells are administered between about 1 day and about 14 days after the HSC graft. In some embodiments, the modified T-cells are administered between about 1 day and about 7 days after the HSC graft. In some embodiments, the modified T-cells are administered between about 2 days and about 4 days after the HSC graft. In some embodiments, the modified T-cells are administered contemporaneously with the HSC graft or within a few hours of the HSC graft (e.g. 1, 2, 3, or 4 hours after the HSC graft).

The modified T-cells may be transfused in a single administration. Alternatively, the modified T-cells may be transfused over a course of multiple administrations. In embodiments where multiple administrations of modified T-cells are made, the same or different amounts of modified T-cells may be transfused at each administration, such as described herein.

Following administration of the modified T-cells, the patient is monitored for the onset of GVHD. Should symptoms arise, MTX may be administered (step 280) to reverse, suppress, or control GVHD. MTX may be administered in a single dose or in multiple doses. If multiple MTX administrations are made, the dosage may be titrated so as to balance GVHD while maintaining some of the protections afforded to the immune system by the modified T-cells.

In some embodiments, an amount of MTX administered ranges from about 2 mg/m$^2$/infusion to about 100 mg/m$^2$/infusion. In some embodiments, an amount of MTX administered ranges from about 2 mg/m$^2$/infusion to about 90 mg/m$^2$/infusion. In some embodiments, an amount of MTX administered ranges from about 2 mg/m$^2$/infusion to about 80 mg/m$^2$/infusion. In some embodiments, an amount of MTX administered ranges from about 2 mg/m$^2$/infusion to about 70 mg/m$^2$/infusion. In some embodiments, an amount of MTX administered ranges from about 2 mg/m$^2$/infusion to about 60 mg/m$^2$/infusion. In some embodiments, an amount of MTX administered ranges from about 2 mg/m$^2$/infusion to about 50 mg/m$^2$/infusion. In some embodiments, an amount of MTX administered ranges from about 2 mg/m$^2$/infusion to about 40 mg/m$^2$/infusion. In some embodiments, an amount of MTX administered ranges from about 2 mg/m$^2$/infusion to about 30 mg/m$^2$/infusion. In some embodiments, an amount of MTX administered ranges from about 20 mg/m$^2$/infusion to about 20 mg/m$^2$/infusion. In some embodiments, an amount of MTX administered ranges from about 2 mg/m$^2$/infusion to about 10 mg/m$^2$/infusion. In some embodiments, an amount of MTX administered ranges from about 2 mg/m$^2$/infusion to about 8 mg/m$^2$/infusion. In other embodiments, an amount of MTX administered ranges from about 2.5 mg/m$^2$/infusion to about 7.5 mg/m$^2$/infusion. In yet other embodiments, an amount of MTX administered is about 5 mg/m$^2$/infusion. In yet further embodiments, an amount of MTX administered is about 7.5 mg/m$^2$/infusion.

In some embodiments, between 2 and 6 infusions are made, and the infusions may each comprise the same dosage or different dosages (e.g. escalating dosages, decreasing dosages, etc.). In other embodiments, between 2 and 4 infusions are made. In some embodiments, the administrations may be made on a weekly basis, or a bi-monthly basis.

Inducement of Graft-Versus-Malignancy in Residual or Recurring Disease

Treatment of hematological malignancies, including leukemia, lymphoma and myeloma, usually involves one or more forms of chemotherapy and/or radiation therapy. These treatments destroy the malignant cells, but also destroy the body's healthy blood cells as well. Allogeneic bone marrow transplantation (BMT) is an effective therapy useful in the treatment of many hematologic malignancies. In allogeneic BMT, bone marrow (or, in some cases, peripheral blood) from an unrelated or a related (but not identical twin) donor is used to replace the healthy blood cells in the cancer patient. The bone marrow (or peripheral blood) contains stem cells, which are the precursors to all the different cell types (e.g., red cells, phagocytes, platelets and lymphocytes) found in blood. It is believed that allogeneic BMT has both a restorative effect and a curative effect. The restorative effect arises from the ability of the stem cells to repopulate the cellular components of blood. The curative properties of allogeneic BMT derive largely from a graft-versus-malignancy (GVM) effect (also referred to as a graft-versus-tumor effect (GVT)). The hematopoietic cells from the donor (specifically, the T lymphocytes) are believed to attack the cancerous cells, enhancing the suppressive effects of the other forms of treatment. Essentially, the GVM effect comprises an attack on the residual tumor cells by the blood cells derived from the BMT, making it less likely that the malignancy will return after transplant.

The efficacy of allogeneic hematopoietic stem cell transplantation for hematologic malignancies is limited by the difficulty in suppressing graft-versus-host disease without compromising graft-versus-malignancy effects. DLI has been used after allotransplant to treat relapsed or residual disease, to convert mixed to full donor chimerism, to restore full immune function as an 'add-back' after T-cell-depleted transplants and to prophylax against relapse as preemptive therapy. Indeed, donor lymphocyte infusion has provided a dramatic example of the potency of GVM, which can induce complete and sustained remissions in many patients even when all cytotoxic therapy has failed. While DLI can be a much safer alternative option than second allogeneic HSCT, GVHD is a common complication resulting in significant morbidity and mortality (see Porter D, Levine J E. Graft-versus-host disease and graft-versus-leukemia after donor leukocyte infusion. Semin Hematol. 2006 January; 43:53-61; Ciceri F, Bordignon C. Suicide-gene-Transduced donor T-cells for controlled graft-versus-host disease and graftversus-tumor. Int J Hematol. 2002 November; 76:305-9). Unfortunately, and as noted herein, acute GVHD has contributed to death in almost 10% of patients. Indeed, in some cases DLI-induced GVHD may be quite severe and, it is believed that between about 20% to about 35% of DLI recipients may develop grade III to IV acute GVHD. As such, it can be said that controlling the GVM effect prevents escalation of the GVM effect into GVHD. Therefore, managing the threat of GVHD while maximizing the beneficial GVM effect would broaden the scope and usefulness of allogenic BMT procedures.

As noted herein, conventional methods of reducing GVHD comprise controlling the number T-cells administered during donor lymphocyte infusion. This method, however, may not only result in a decreased GVM effect and a slower immune recovery, but may also cause increased rates of graft rejection. To combat this, in some aspects of the present disclosure are methods of treating cancer by stimulating or encouraging a GVM effect by administering lymphocytes to the patient that have been modified so as to be at least partially HPRT-deficient, and then monitoring for the onset of GVHD. At the onset of GVHD, one or more therapeutically effective doses of MTX may be administered to suppress, reduce, control, or otherwise mitigate GVHD. In some embodiments, a single dosage of MTX is administered. In other embodiments, the amount of MTX administered depends upon the severity of the onset of GVHD and, in that regard, the dose (or dosages) of MTX may be titrated to achieve a desired reduction in GVHD symptoms (again, with the intent to balance any GVM effect). In some embodiments, the GVM is a graft-versus-leukemia effect (GVL). In some embodiments, the modified T-cells are provided during a single administration. In other embodiments, multiple administrations of the modified T-cells are provided. In some embodiments, the modified T-cells are produced according to the methods (steps 110 through 140) described herein, such as illustrated in FIG. 1.

Figure 3:
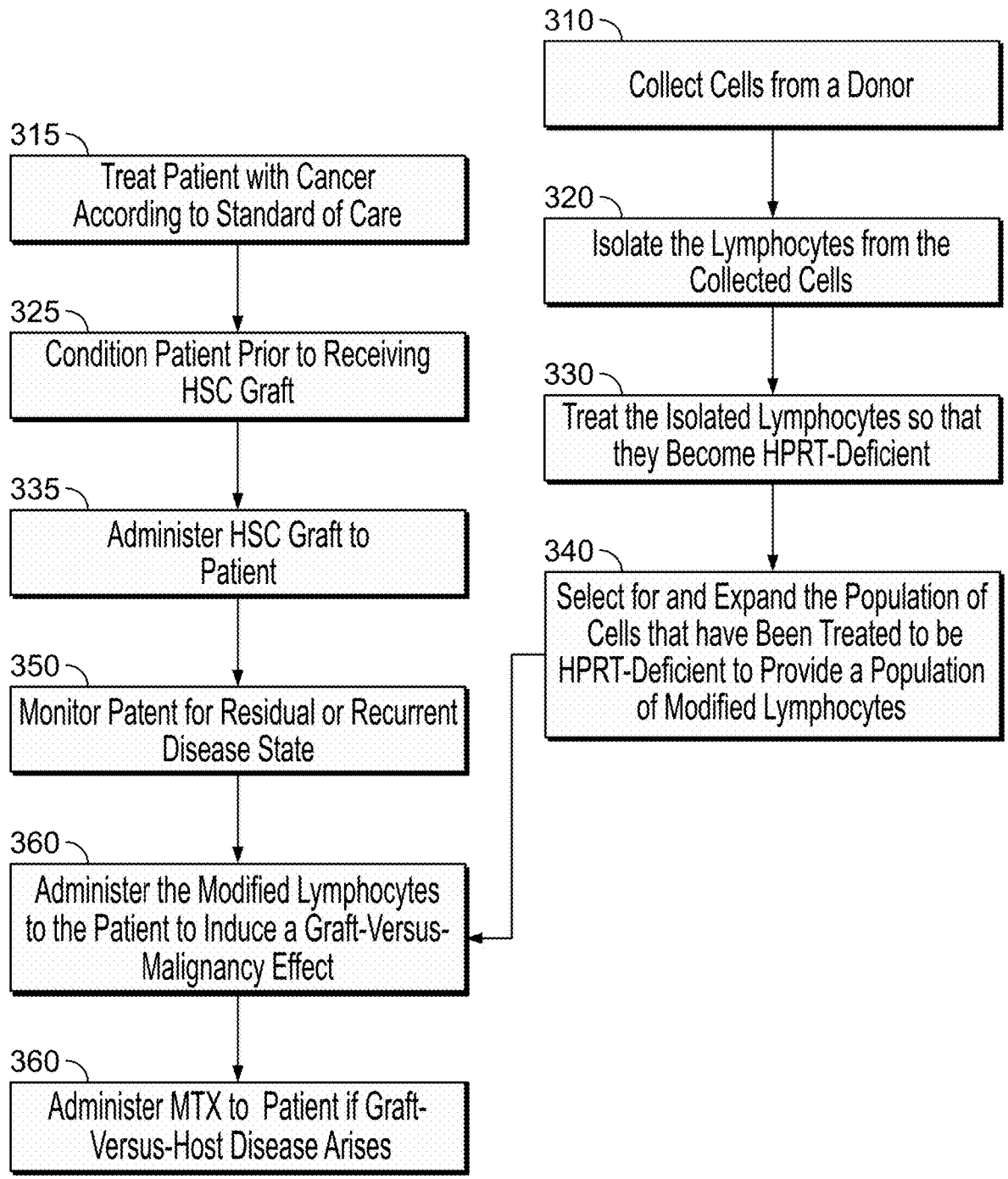
FIG. 3 is a flow chart illustrating the steps of preparing modified T-cells and administering those modified T-cells to a patient following a stem cell graft, such that the modified T-cells assist in inducing the GVM effect.

FIG. 3 illustrates one method of reducing, suppressing, or controlling GVHD upon onset of symptoms. Initially, cells are collected from a donor at step 310. The cells may be collected from the same donor that provided the HSC for grafting (see step 335) or from a different donor. Lymphocytes are then isolated from the collected cells (step 320) and treated such that they become HPRT-deficient (step 330). Methods of treating the isolated cells are set forth herein. To arrive at a population of modified T-cells that are HPRT deficient, the treated cells are selected for and expanded (step 340), such as described herein. The modified T-cells are then stored for later use.

A patient having cancer, for example a hematological cancer, may be treated according to the standard of care available to the patient at the time of presentation and staging of the cancer (e.g. radiation and/or chemotherapy, including biologics) (step 315). The patient may also be a candidate for HSC transplantation and, if so, a conditioning regimen (step 325) is implemented (e.g. by high-dose conditioning radiation or chemotherapy). It is believed that for malignancy, one wishes to "wipe out" the blood system completely, or as close to completely as possible, thus, to killing off as many malignant cells as possible. The goals of such a conditioning regimen being to treat the cancer cells intensively, thereby making a cancer recurrence less likely, inactivate the immune system to reduce the chance of a stem cell graft rejection, and enable donor cells to travel to the marrow. In some embodiments, conditioning includes administration of one or more of cyclophosphamide, cytarabine (AraC), etoposide, melphalan, busulfan, or high-dose total body irradiation. The patient is then treated with an allogenic HSC graft (step 335). In some embodiments, the allogenic HSC graft induces at least a partial GVM, GVT, or GVL effect.

Following grafting, the patient is monitored (step 350) for residual or recurrent disease. Should such residual or recurrent disease present itself, the modified T-cells (produce at step 340) are administered to the patient (step 360) such that a GVM, GVT, or GVT effect may be induced. The modified T-cells may be infused in a single administration of over a course of several administrations. In some embodiments, the modified T-cells are administered between about 1 day and about 21 days after the HSC graft. In some embodiments, the modified T-cells are administered between about 1 day and about 14 days after the HSC graft. In some embodiments, the modified T-cells are administered between about 1 day and about 7 days after the HSC graft. In some embodiments, the modified T-cells are administered between about 2 days and about 4 days after the HSC graft. In some embodiments, the modified T-cells are administered contemporaneously with the HSC graft or within a few hours of the HSC graft (e.g. 1, 2, 3, or 4 hours after the HSC graft).

Should symptoms of GVHD arise, MTX is administered to the patient, either in a single dose or over multiple doses. In some embodiments, the amount of MTX administered depends upon the severity of the onset of GVHD and, in that regard, the dose (or dosages) of MTX may be titrated to achieve a desired reduction in GVHD symptoms and/or a desired level of the GVM, GVT, or GVL effect.

In some embodiments, an amount of MTX administered ranges from about 2 $mg/m^2$/infusion to about 100 $mg/m^2$/infusion. In some embodiments, an amount of MTX administered ranges from about 2 $mg/m^2$/infusion to about 90 $mg/m^2$/infusion. In some embodiments, an amount of MTX administered ranges from about 2 $mg/m^2$/infusion to about 80 $mg/m^2$/infusion. In some embodiments, an amount of MTX administered ranges from about 2 $mg/m^2$/infusion to about 70 $mg/m^2$/infusion. In some embodiments, an amount of MTX administered ranges from about 2 $mg/m^2$/infusion to about 60 $mg/m^2$/infusion. In some embodiments, an amount of MTX administered ranges from about 2 $mg/m^2$/infusion to about 50 $mg/m^2$/infusion. In some embodiments, an amount of MTX administered ranges from about 2 $mg/m^2$/infusion to about 40 $mg/m^2$/infusion. In some embodiments, an amount of MTX administered ranges from about 2 $mg/m^2$/infusion to about 30 $mg/m^2$/infusion. In some embodiments, an amount of MTX administered ranges from about 20 $mg/m^2$/infusion to about 20 $mg/m^2$/infusion. In some embodiments, an amount of MTX administered ranges from about 2 $mg/m^2$/infusion to about 10 $mg/m^2$/infusion. In some embodiments, an amount of MTX administered ranges from about 2 $mg/m^2$/infusion to about 8 $mg/m^2$/infusion. In other embodiments, an amount of MTX administered ranges from about 2.5 $mg/m^2$/infusion to about 7.5 $mg/m^2$/infusion. In yet other embodiments, an amount of MTX administered is about 5 $mg/m^2$/infusion. In yet further embodiments, an amount of MTX administered is about 7.5 $mg/m^2$/infusion.

In some embodiments, between 2 and 6 infusions are made, and the infusions may each comprise the same dosage or different dosages (e.g. escalating dosages, decreasing dosages, etc.). In some embodiments, the administrations may be made on a weekly basis, or a bi-monthly basis.

A Modulatable Switch for Use in Selection and Deselection of Chimeric Antigen Receptor (CAR) Modified T-Cells Chimeric antigen receptors (CARs) are designed for adoptive immunotherapy by connecting an extracellular antigen-binding domain to a transmembrane domain and an intracellular signaling domain (endodomain). It is a useful anti-tumor approach to eradicate tumor cells by adoptive transfer of T-cells expressing chimeric antigen receptors to recognize specific antigens presented on tumor cells and activate T-cells to specifically lyse these tumor cells. A critical aspect of this CAR strategy is the selection of target epitopes that are specifically or selectively expressed on tumors, are present on all tumor cells, and are membrane epitopes not prone to shed or modulate from the cell surface. However, ideally the CART T cells would be able to be used as a universal reagent or drug suitable for any mammalian (such as human) recipient. To employ the cells in such a manner, one must prevent their rejection in a graft-versus-host response without compromising CAR-dependent effector functions.

One drawback to the use of CAR-T cells in subjects has been the initiation of Cytokine Release Syndrome (CRS) in some recipients. Cytokine-associated toxicity, also referred to as a "cytokine storm" or more recently as cytokine release syndrome (CRS), is a common and potentially lethal complication of CAR-T cell therapy. CRS is a non-antigen specific toxicity that can occur as a result of the high-levels of CAR-T cell expansion and immune activation typically required to mediate clinical benefit using modern immunotherapies such as CAR-T cell transfer. Timing of symptom onset and CRS severity depends on the inducing agent and the magnitude of immune cell activation. Symptom onset typically occurs days to occasionally weeks after T-cell infusion, coinciding with maximal in vivo T-cell expansion. In recent reports of CRS following adoptive T-cell therapy for cancer, the incidence and severity of the syndrome is greater when patients have large tumor burdens, due to the expression of production of proinflammatory cytokines such as TNF-cc by the adoptively transferred expanding and activated CAR-T cell populations. CRS associated with adoptive T-cell therapies has been consistently associated with elevated IFNy, IL-6, and TNFa levels, and increases in IL-2, granulocyte macrophage-colony-stimulating factor (GM-CSF), IL-10, IL-8, IL-5, and fracktalkine have also been reported.

Figure 4:
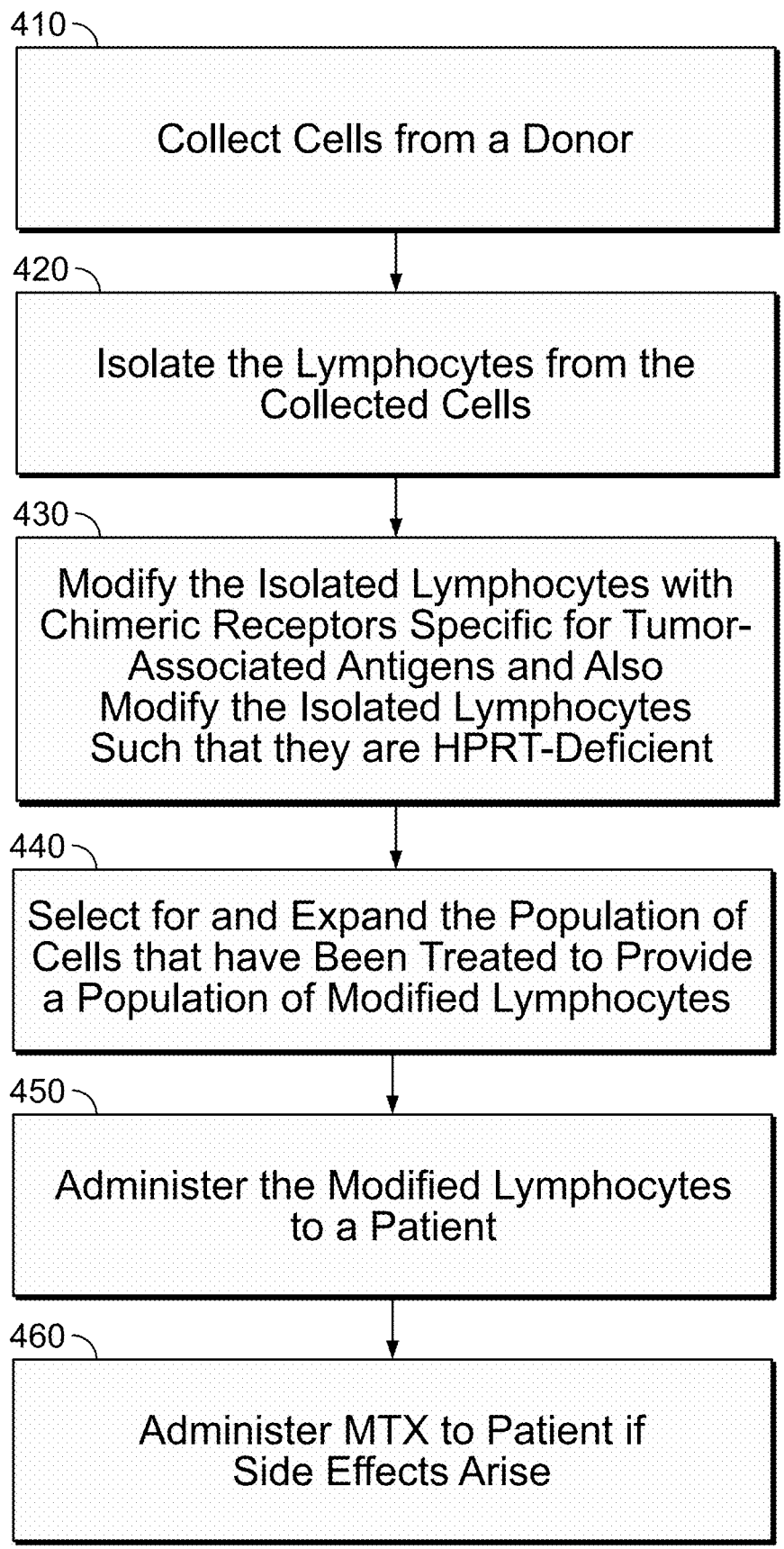
FIG. 4 is a flow chart illustrating the steps of preparing modified T-cells (CAR-T cells that are HRPT-deficient) and administering those modified T-cells to a patient in need thereof.

In another aspect of the present disclosure is a method of treating a patient having cancer by administering modified CAR T cells to a patient in need thereof, the modified CAR T cells being HPRT-deficient. FIG. 4 illustrates one method of treating a patient having cancer and subsequently reducing, suppressing, or controlling any deleterious side effects. Initially, cells are collected from a donor at step 410. Lymphocytes are then isolated from the collected cells (step 420) and modified to provide CAR T-cells that are HPRT-deficient.

Genetic modification for introduction of the CAR construct into T-cells can be accomplished by transducing (or otherwise delivering) a T-cell composition with a recombinant DNA or RNA construct, such as for example, a vector. The appropriate DNA sequence may be inserted into the vector by a variety of procedures but, in general, the DNA sequence is inserted into an appropriate restriction endonuclease site(s) by procedures known in the art. In addition to the introduction of the CAR construct, the shRNA to knockout the HPRT gene may also be included (such as described herein) other methods which may be used to concurrently knock-out HPRT activity.

As described in U.S. Pat. Nos. 5,359,046, 5,686,281 and 6,103,521 (the disclosures of which are hereby incorporated by reference herein in their entireties), the extracellular domain of the chimeric receptor may be obtained from any of the wide variety of extracellular domains or secreted proteins associated with ligand binding and/or signal transduction. The extracellular domain may be part of a protein which is monomeric, homodimeric, heterodimeric, or associated with a larger number of proteins in a non-covalent complex. In particular, the extracellular domain may consist of an Ig heavy chain which may in turn be covalently associated with Ig light chain by virtue of the presence of CHI and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used, or a truncated chain may be used, where all or a part of the CHI, CH2, or CH3 domains may be removed or all or part of the hinge region may be removed.

The extracellular domains of CARs are often derived from immunoglobulins. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

When an antitumor chimeric receptor is utilized, the tumor may be of any kind provided it has a cell surface antigen which may be recognized by the chimeric receptor. In a specific embodiment, the chimeric receptor may be for any cancer for which a specific monoclonal antibody exists or is capable of being generated. In particular, cancers such as neuroblastoma, small cell lung cancer, melanoma, ovarian cancer, renal cell carcinoma, colon cancer, Hodgkin's lymphoma, and acute lymphoblastic leukemia (e.g., childhood acute lymphoblastic leukemia) have antigens which may be targeted by the chimeric receptors. The compositions and methods of this can be used in immunotherapy in the treatment of cancer, in particular the treatment of lung cancer, melanoma, breast cancer, prostate cancer, colon cancer, renal cell carcinoma, ovarian cancer, neuroblastoma, rhabdomyosarcoma, leukemia and lymphoma. The compositions and methods described in the present may be utilized in conjunction with other types of therapy for cancer, such as chemotherapy, surgery, radiation, gene therapy, and so forth, as described hereinafter.

To arrive at a population of modified CAR T-cells that are HPRT deficient, the treated cells are selected for and expanded (step 440), such as described herein. The modified CAR T-cells that are HPRT deficient may be administered (step 450) to the patient so as to target certain tumor cells. Should any side effects of CAR T T therapy arise, MTX may be administered to the patient (460) to suppress, reduce, or control the side effects. In some embodiments, the amount of MTX administered depends upon the type and/or severity of the side effects and, in that regard, the dose (or dosages) of MTX may be titrated to achieve a desired reduction in the side effects presented.

In some embodiments, an amount of MTX administered ranges from about 2 mg/m$^2$/infusion to about 100 mg/m$^2$/infusion. In some embodiments, an amount of MTX administered ranges from about 2 mg/m$^2$/infusion to about 90 mg/m$^2$/infusion. In some embodiments, an amount of MTX administered ranges from about 2 mg/m$^2$/infusion to about 80 mg/m$^2$/infusion. In some embodiments, an amount of MTX administered ranges from about 2 mg/m$^2$/infusion to about 70 mg/m$^2$/infusion. In some embodiments, an amount of MTX administered ranges from about 2 mg/m$^2$/infusion to about 60 mg/m$^2$/infusion. In some embodiments, an amount of MTX administered ranges from about 2 mg/m$^2$/infusion to about 50 mg/m$^2$/infusion. In some embodiments, an amount of MTX administered ranges from about 2 mg/m$^2$/infusion to about 40 mg/m$^2$/infusion. In some embodiments, an amount of MTX administered ranges from about 2 mg/m$^2$/infusion to about 30 mg/m$^2$/infusion. In some embodiments, an amount of MTX administered ranges from about 20 mg/m$^2$/infusion to about 20 mg/m$^2$/infusion. In some embodiments, an amount of MTX administered ranges from about 2 mg/m$^2$/infusion to about 10 mg/m$^2$/infusion. In some embodiments, an amount of MTX administered ranges from about 2 mg/m$^2$/infusion to about 8 mg/m$^2$/infusion. In other embodiments, an amount of MTX administered ranges from about 2.5 mg/m$^2$/infusion to about 7.5 mg/m$^2$/infusion. In yet other embodiments, an amount of MTX administered is about 5 mg/m$^2$/infusion. In yet further embodiments, an amount of MTX administered is about 7.5 mg/m$^2$/infusion.

In some embodiments, between 2 and 6 infusions are made, and the infusions may each comprise the same dosage or different dosages (e.g. escalating dosages, decreasing dosages, etc.). In some embodiments, the administrations may be made on a weekly basis, or a bi-monthly basis.

A Modulatable Switch for Use in Selection and Deselection of T-cell Receptor Modified (TCR) T-cells The present disclosure is also directed to methods of reducing or ameliorating, or preventing or treating, diseases and disorders using TCR-modified T-cells that are also HPRT deficient. Initially, cells are collected from a donor. Lymphocytes are then isolated from the collected cells and modified to provide TCR-modified T-cells that are HPRT deficient. Should any side effects of TCR-modified T-cell therapy arise, MTX may be administered to the patient to suppress, reduce, or control the side effects.

T-cells (also known as T lymphocytes) are found widely distributed within tissues and the tumor environment. They play a central role in cell-mediated immunity and can mediate long-lived, antigen-specific, effector and immune memory responses. T-cells are distinguished from other lymphocytes by the presence of T-cell receptors (TCRs) on the cell surface. The TCR is a multi-subunit transmembrane complex that mediates the antigen-specific activation of T-cells. The TCR is composed of two different polypeptide chains, the TCR α and β chains. Both chains have an N-terminal variable region and a constant region. The chains are linked by a disulphide bond, with each receptor providing a single antigen-binding site. Stimulation of the TCR is triggered by major histocompatibility complex molecules (MHC) (proteins that control immune responses, encoded by a genetic locus encompassing a family of highly polymorphic genes) on antigen presenting cells that present antigen peptides to the T-cells and bind to the TCR complexes to induce a series of intracellular signaling cascades.

More specifically, the TCR is generally composed of six different membrane bound chains that form the TCR heterodimer responsible for ligand recognition. TCRs exist in alpha/beta and gamma/delta forms, which are structurally similar but have distinct anatomical locations and functions. In one embodiment, the TCR comprises a TCR alpha and beta chain, such as the nucleic acid encoding the TCR comprises a nucleic acid encoding a TCR alpha and a TCR beta chain. In another embodiment, an alpha or beta chain or both comprises at least one N-deglycosylation. Each chain is composed of two extracellular domains, a variable and constant domain. In one embodiment, the TCR comprises at least one murine constant region. The constant domain is proximal to the cell membrane, followed by a transmembrane domain and a short cytoplasmic tail. In one embodiment, the co-stimulatory signaling domain is a 4-IBB co-stimulatory signaling domain. The variable domain contributes to the determination of the particular antigen and MHC molecule to which the TCR has binding specificity. In turn, the specificity of a T-cell for a unique antigen-MHC complex resides in the particular TCR expressed by the T-cell. Each of the constant and variable domains may include an intra-chain disulfide bond. In one embodiment, TCR comprises at least one disulfide bond. The variable domains include the highly polymorphic loops analogous to the complementarity determining regions (CDRs) of antibodies. The diversity of TCR sequences is generated via somatic rearrangement of linked variable (V), diversity (D), joining (J), and constant genes. Functional alpha and gamma chain polypeptides are formed by rearranged V-J-C regions, whereas beta and delta chains consist of V-D-J-C regions. The extracellular constant domain includes a membrane proximal region and an immunoglobulin region.

The TCR confers antigenic specificity on the T-cell, by recognizing an antigen ligand comprising a short contiguous amino acid sequence of a protein that is presented on the target cell by a major histocompatibility complex molecule. Accessory adhesion molecules expressed by T-cells, such as CD4 for MHC class II and CD8 for MHC class I, are also involved. The TCR interacts with this ligand by making contacts with both the MHC molecule and the antigen peptide. Signal transduction is through the associated invariant CD3 complex, which is composed of four different CD3 proteins that form two heterodimers (CD3δε and CD3γε) and one homodimer (CD3ζζ).

Following contact with their cognate peptides presented by MHC class I molecules, naive CD8+ cytotoxic T-cells proliferate vigorously and acquire phenotypic and functional properties allowing them to act as effector T-cells; these eliminate cells expressing the antigen, through apoptosis-inducing ligands or release of lytic granules. In addition, long-lasting memory T-cells are generated that can self-renew, allowing rapid expansion in the presence of the target antigen and providing a sustained and durable response to it upon re-exposure. The function of T-cells as orchestrators and effectors of the adaptive immune response is directed by the specificity of the TCR.

T-cells internalize, sort, and degrade the entire T-cell receptor as a complex, with a half-life of about 10 hours in resting T-cells and 3 hours in stimulated T-cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T-cell, which all must signal properly. Thus, if a TCR complex is destabilized with proteins that do not associate properly or cannot signal optimally, the T-cell will not become activated sufficiently to begin a cellular response.

Genetically modified TCR therapies are based on altering T-cell specificity through the expression of specific TCR α and β chains, which mediate the antigen-recognition process. The tumor-specific TCR α and β chains are identified, isolated and cloned into transduction vectors and transduction of T-cells creates tumor-antigen-specific T-cells. In some embodiments, TCR expression is modified using shRNAs that target nucleic acids encoding specific TCRs (e.g., TCR-α and TCR-β) and/or CD3 chains in primary T-cells. By blocking expression of one or more of these proteins, the T-cell will no longer produce one or more of the key components of the TCR complex. Expression of shRNAs in primary T-cells can be achieved using any conventional expression system, e.g., a lentiviral expression system. TCR-alpha, TCR-beta, TCR-gamma, TCR-delta, CD3-gamma, CD3-delta, CD3-epsilon, or CD3-zeta mRNAs can be targeted separately or together using a variety of targeting shRNAs. In some embodiments, the genetically modified TCR T-cells are rendered HPRT deficient, such as by knocking down the HPRT gene with an anti-HPRT shRNA as described herein.

In other embodiments, to generate a successful tumor-specific TCR, an appropriate target sequence is first identified. This might be isolated from a rare tumor-reactive T-cell or, where this is not possible, alternative technologies can be employed to generate highly active anti-tumor T-cell antigens. One approach is to immunize transgenic mice that express the human leukocyte antigen (HLA) system with human tumor proteins to generate T-cells expressing TCRs against human antigens (Stanislawski et al., 2001). An alternative approach is allogeneic TCR gene transfer, in which tumor-specific T-cells are isolated from a patient experiencing tumor remission and the reactive TCR sequences are transferred to T-cells from another patient who shares the disease but is non-responsive (Gao et al., 2000; de Witte et al., 2006). Finally, in vitro technologies can be employed to alter the sequence of the TCR, enhancing their tumor-killing activity by increasing the strength of the interaction (avidity) of a weakly reactive tumor-specific TCR with target antigen (Robbins et al., 2008; Schmid et al., 2010).

Following generation of the genetically modified TCR T-cells, the modified cells are administered to a patient in need of treatment thereof. If side effects arise from treatment, MTX may be administered to lessen or eradicate such side effects (e.g. GVHD or symptoms of GVHD). In some embodiments, an amount of MTX administered ranges from about 2 mg/m$^2$/infusion to about 100 mg/m$^2$/infusion. In some embodiments, an amount of MTX administered ranges from about 2 mg/m$^2$/infusion to about 90 mg/m$^2$/infusion. In some embodiments, an amount of MTX administered ranges from about 2 mg/m$^2$/infusion to about 80 mg/m$^2$/infusion. In some embodiments, an amount of MTX administered ranges from about 2 mg/m$^2$/infusion to about 70 mg/m$^2$/infusion. In some embodiments, an amount of MTX administered ranges from about 2 mg/m$^2$/infusion to about 60 mg/m$^2$/infusion. In some embodiments, an amount of MTX administered ranges from about 2 mg/m$^2$/infusion to about 50 mg/m$^2$/infusion. In some embodiments, an amount of MTX administered ranges from about 2 mg/m$^2$/infusion to about 40 mg/m$^2$/infusion. In some embodiments, an amount of MTX administered ranges from about 2 mg/m$^2$/infusion to about 30 mg/m$^2$/infusion. In some embodiments, an amount of MTX administered ranges from about 20 mg/m$^2$/infusion to about 20 mg/m$^2$/infusion. In some embodiments, an amount of MTX administered ranges from about 2 mg/m$^2$/infusion to about 10 mg/m$^2$/infusion. In some embodiments, an amount of MTX administered ranges from about 2 mg/m$^2$/infusion to about 8 mg/m$^2$/infusion. In other embodiments, an amount of MTX administered ranges from about 2.5 mg/m$^2$/infusion to about 7.5 mg/m$^2$/infusion. In yet other embodiments, an amount of MTX administered is about 5 mg/m$^2$/infusion. In yet further embodiments, an amount of MTX administered is about 7.5 mg/m$^2$/infusion.

In some embodiments, between 2 and 6 infusions are made, and the infusions may each comprise the same dosage or different dosages (e.g. escalating dosages, decreasing dosages, etc.). In some embodiments, the administrations may be made on a weekly basis, or a bi-monthly basis.

EXAMPLES

Example 1

CAR-T cells are produced by infecting the cells with the CAR construct in tandem with the shRNA to HPRT. This is in a single lentiviral vector with the CAR and shRNA driven by different promoters (Pol II and Pol III respectively). It is believed that if the shRNA targeting HPRT is within a miRNA framework, it could also be expressed from a Pol II promoter (maybe even the same promoter).

The transduced CAR-T shHPRT cells are then infused into a leukemic patient and anti-leukemia response monitored while if needed, expanding the CAR-T shHPRT cells with 6TG. Once the effect is impacting, a turn-off strategy using methotrexate to kill the transduced CAR-T shHPRT cells can be contemplated. This kill-off strategy is put into place if an inflammatory response or undue clonal proliferation of the CAR-T shHPRT cells is seen. It should be noted that some anti-leukemia antigens are also present on normal healthy cells and may give an untoward effect. Thus, applying this selection/suicide strategy increases efficacy/safety profile.

Example 2

In allogeneic bone marrow transplant for hematological malignancy, donor T-cells are included with bone marrow transplant for an anti-tumor effect. This is important to eliminate residual disease following pre-transplant conditioning. In this example the donor T-cells are transduced with a lentiviral vector containing shRNA to HPRT before infusion and once infused the donor T-cell impact is assessed. As the Graft vs Leukemia (GVL) effect is monitored, if there is consequent Graft versus host disease (GVHD) this can be ameliorated using the "kill" switch with methotrexate. This allows GVL without consequent GVHD.

Example 3

In allogeneic bone marrow transplantation there is a delayed immune recovery with a risk of adventitious agent infection. To guard against this and maintain T-cell activity, donor T-cells are given that have been transduced with a lentiviral vector containing HPRT. Over time this will provide ancillary control over potential infections until T-cells derived from the bone marrow transplanted stem cell reconstitute the hematopoietic system. If there is untoward inflammatory response or any other donor T-cell related AE they are eliminated using methotrexate. This allows anti-infection immune control without GVHD.

Example 4

A patient has a leukemia. His own or matched allogeneic T-cells are taken and grown in tissue culture with growth supporting cytokines, e.g. IL2 or IL7, during which time they are transduced (infected leading to transgene expression) with a self-inactivating lentiviral vector that contains three elements i.e. tumor targeting, cell lysis machinery and a vector including components to knockdown HPRT. These gene-modified cells at $1\times10^6$ to $2\times10^8$ cells/sq meter are infused into the patient after a dose of IV Cytoxan, e.g. at 500 mg/sq meter IV (to make space for the introduced CAR-T cells). In this example the gene-modified CAR-T cells have some effect on leukemia. The leukemic cell burden is monitored, e.g. by differential blood counts, and if the physician desires more tumor cell killing, 0.4 mg/kg 6TG is given to the patient IV to increase the relative number of tumor-targeted CAR-T cells by selecting for these cells. If the CAR-T cells exert their positive anti-leukemia effect but there is an "over activation" leading to, e.g. inflammatory cytokine storm, then the reverse can occur in which the CAR-T cells are killed off using IV infusion of methotrexate, e.g. at 100 mg total dose.

Example 5

HPRT Knockdown Versus Knockout with 6TG Selection

Figure 9A:
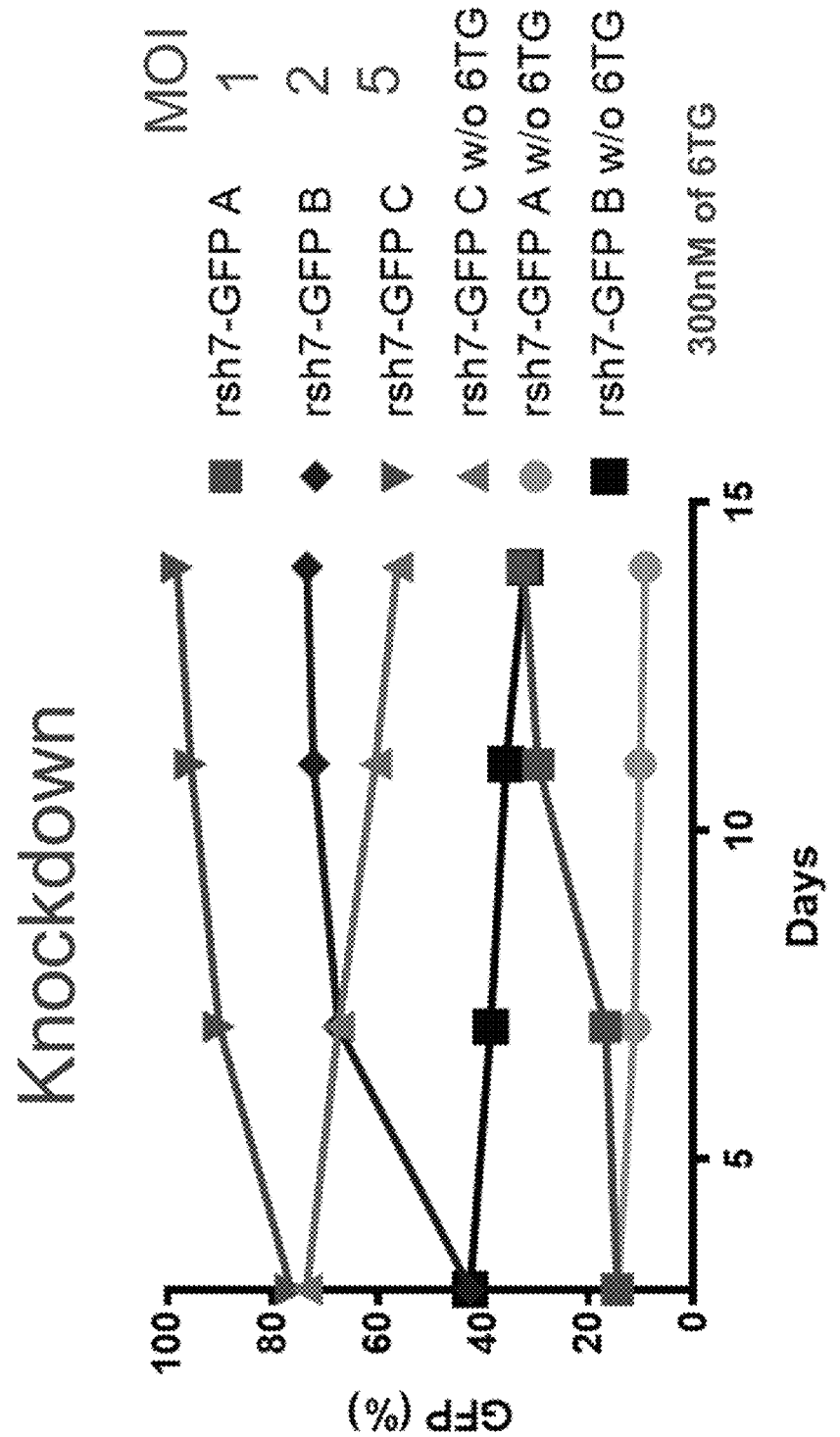
FIGS. 9A and 9B illustrate the effect of positive selection with 6TG (ex vivo) on K562 cells.
Figure 9B:
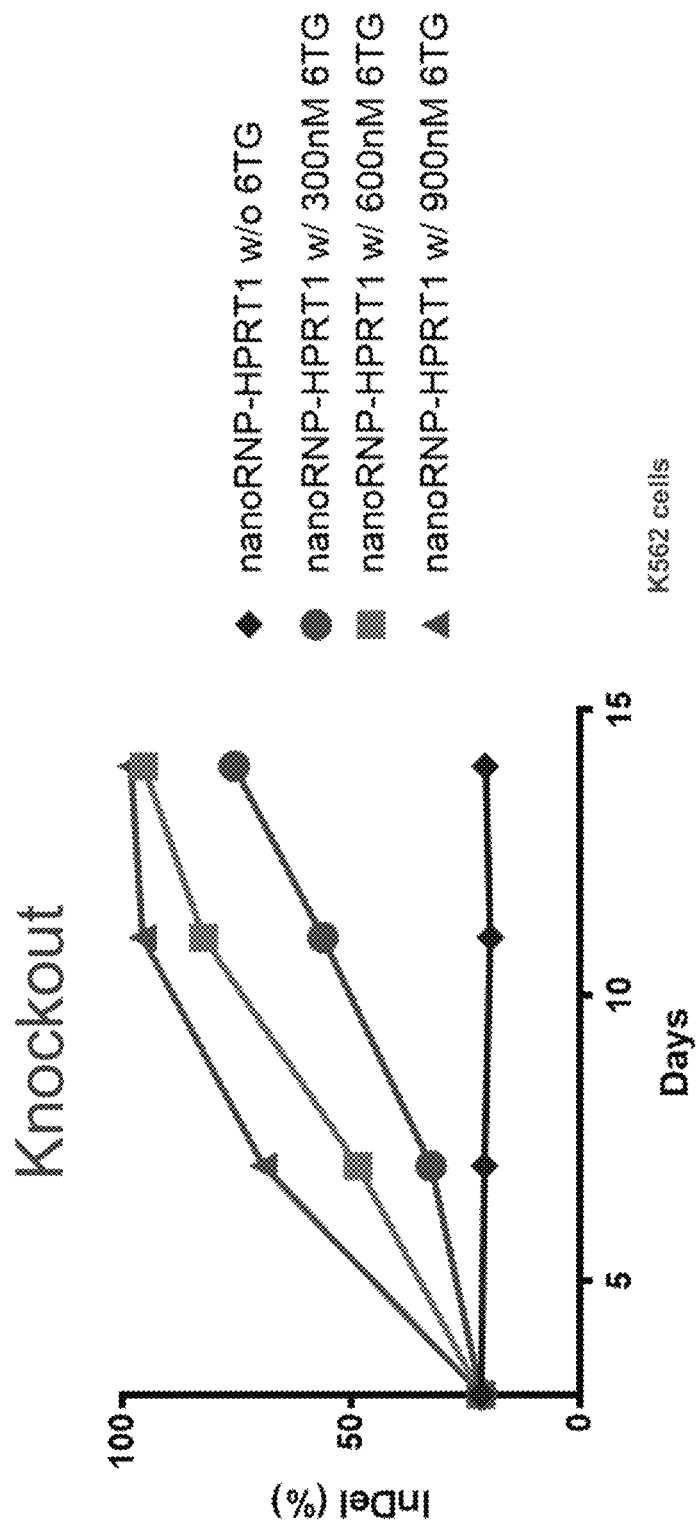

K562 cells were transduced with a vector including a nucleic acid sequence designed to knockdown HPRT and a nucleic acid sequence encoding the green fluorescent protein (GFP) (MOI=1/2/5); or were transfected with a nanocapsule including CRISPR/Cas9 and a sgRNA to HPRT (100 ng/5× $10^4$ cells) at day zero (0). 6-TG was added into the medium from day 3 through day 14. The medium was refreshed every 3 to 4 days. GFP was analyzed on flow machine and InDel % as analyzed with T7E1 assay. FIG. 9A illustrates that the GFP+ population of transduced K562 cells increased from day 3 to day 14 under treatment of 6TG; while the GFP+ population was almost steady without 6-TG treatment. FIG. 9B illustrates that HPRT knockout population of K562 cells increased from day 3 to day 14 under treatment of 6TG and higher dosages (900 nM) of 6TG led to faster selection as compared with a dosage of 300/600 nM of 6TG. It should be noted that 6TG selection process occurred much faster on HPRT knockout cells as compared with the HPRT knockdown cells (MOI=1) at the same concentration of 300 nM of 6TG from day 3 to day 14. The difference between knockdown and knockout could be explained by some level of residual HPRT by the RNAi knockdown approach as compared with the full elimination of HPRT by the knockout approach. Therefore, HPRT-knockout cells were believed to have a much higher tolerance against 6TG and are believed to grow much faster at higher dosages of 6TG (900 nM) compared with HPRT-knockdown cells.

Figure 10A:
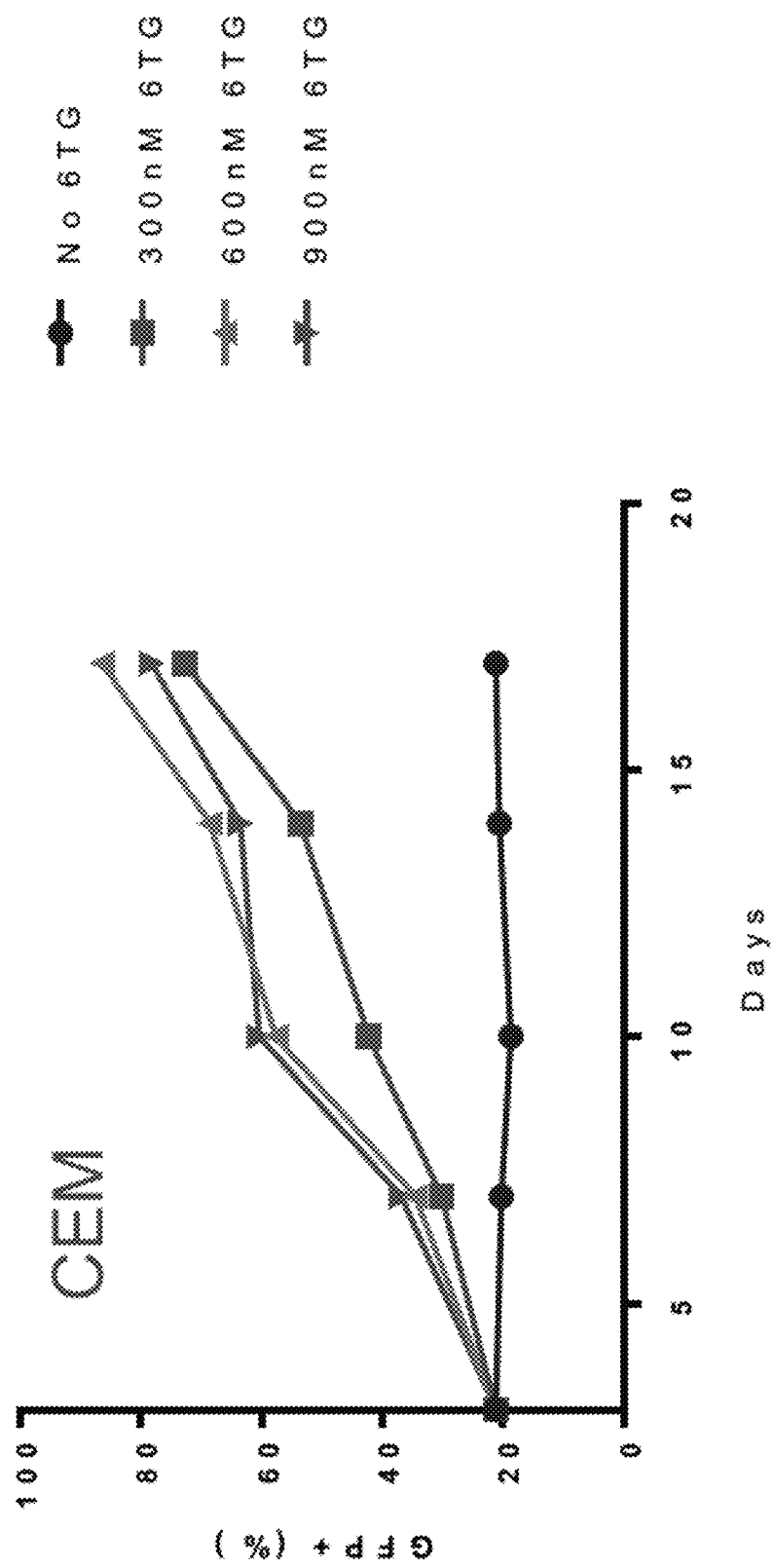

CEM cells were transduced with a vector including a nucleic acid sequence designed to knockdown HPRT and a nucleic acid sequence encoding the green fluorescent protein or transfected with a nanocapsule including CRISPR/Cas9 and a sgRNA to HPRT at day 0. 6-TG was added into the medium from day 3 to day 17. The medium was refreshed every 3 to 4 days. GFP as analyzed on flow machine and InDel % is analyzed by T7E1 assay. FIG. 10A illustrates that the GFP+ population of transduced K562 cells increased from day 3 to day 17 under treatment of 6TG while GFP+ population was almost steady without 6-TG. FIG. 10B shows that HPRT knockout population of CEM cells increased from day 3 to 17 under treatment of 6TG and that a higher dosage (900 nM) of 6TG leads to a faster selection as compared with a dosage of 300/600 nM of 6TG. It should be noted that 6TG selection process occurred faster on HPRT knockout cells rather than HPRT knockdown cells (MOI=1) at the same concentration of 6TG from day 3 to day 17.

Example 6

Negative Selection with MTX or MPA

Figure 11A:
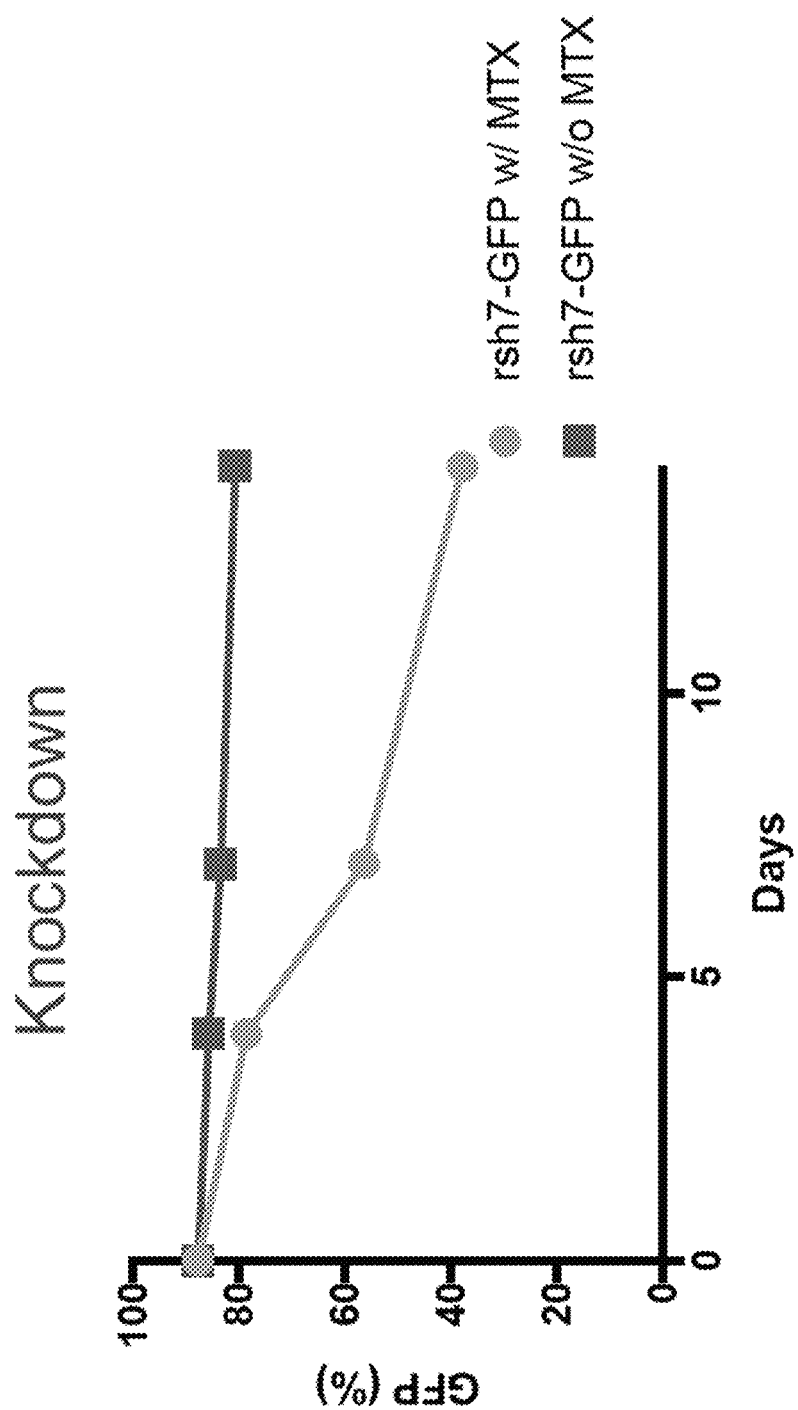
FIGS. 11A and 11B illustrate the effect of negative selection with MTX on K562 cells.
Figure 11B:
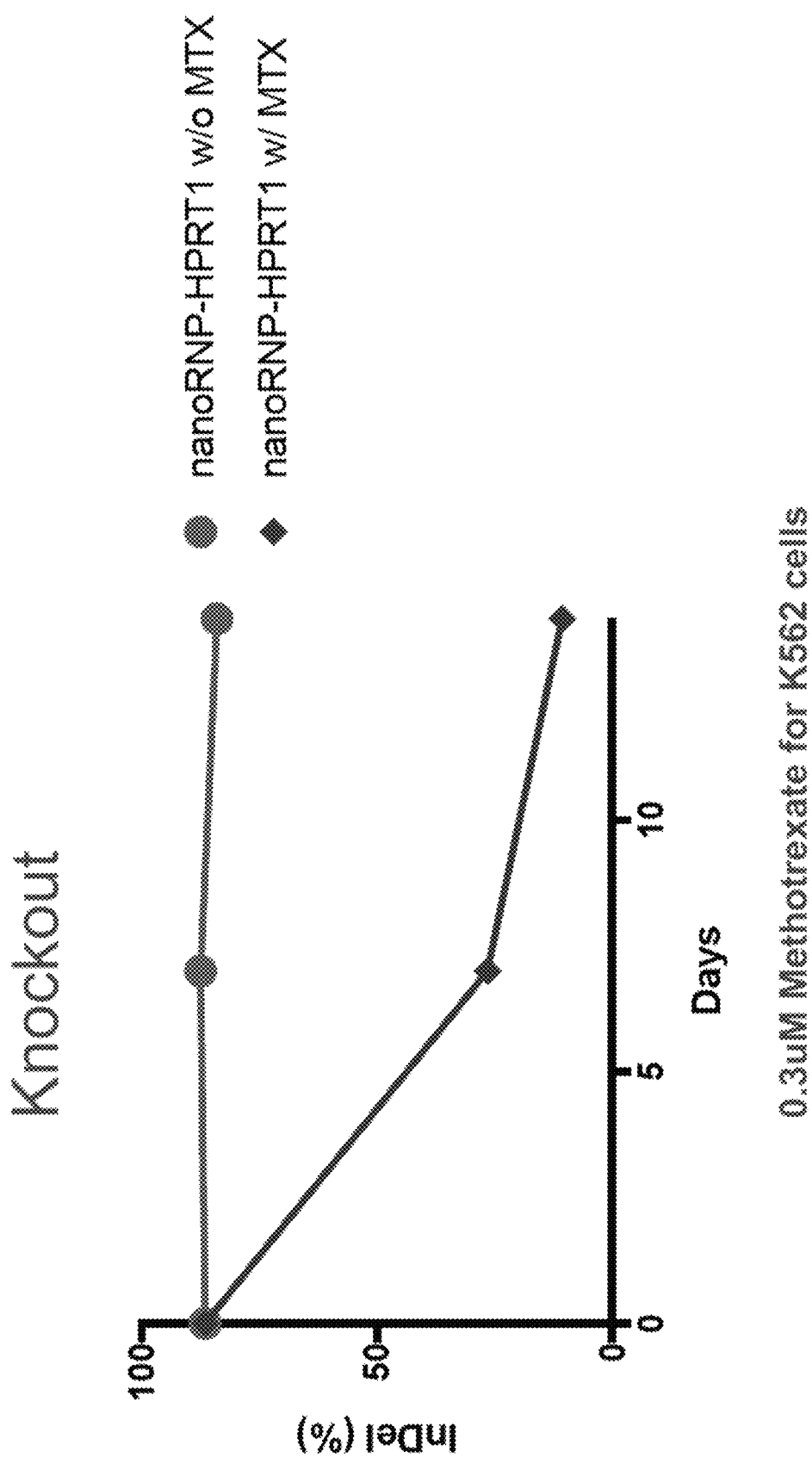
Figure 12B:
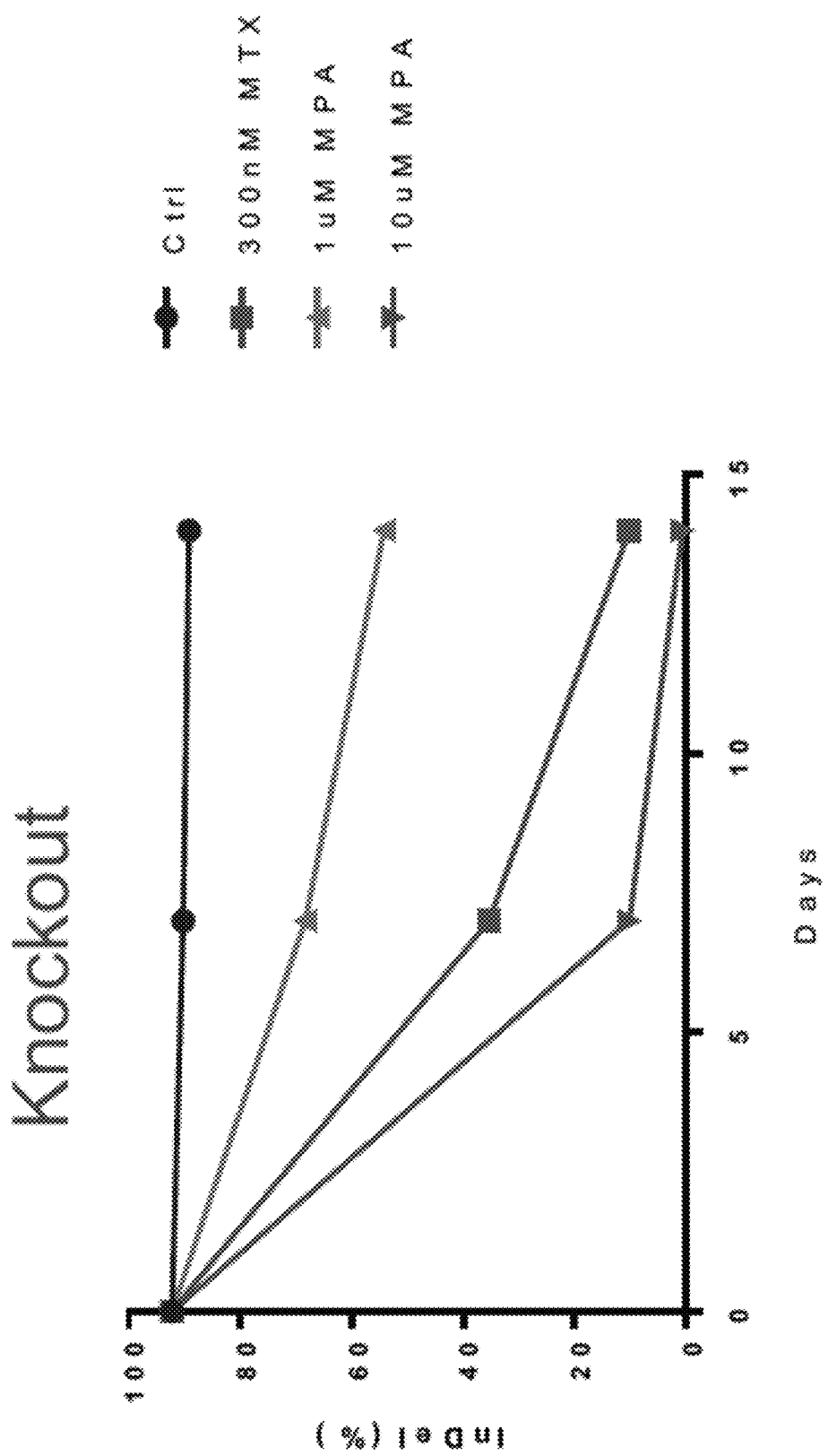

Transduced or transfected K562 cells (such as those from Example 6) were cultured with or without MTX from day 0 to day 14. The medium was refreshed every 3 to 4 days. GFP was analyzed on flow machine and InDel % was analyzed by T7E1 assay. FIG. 11A shows that the GFP-population of transduced K562 cells decreased under the treatment of 0.3 uM of MTX the population of cells was steady without MTX. FIG. 11B illustrates that the transfected K562 cells were eliminated under treatment with 0.3 uM of MTX at a faster pace as compared with the HPRT-KD population.

Transduced or transfected CEM cells (such as those from Example 6) were cultured with or without MTX from day 0 to day 14. The medium was refreshed every 3 to 4 days. GFP was analyzed on flow machine and InDel % was analyzed by T7E1 assay. FIG. 121A shows the GFP-population of transduced K562 decreased under the treatment of 1 uM of MPA or 0.3 uM of MTX or 10 uM of MPA while the population of cells was steady for the untreated group. FIG>12B illustrates that the HPRT knockout population of CEM cells were eliminated at a faster pace under the treatment of 1 uM of MPA or 0.3 uM of MTX or 10 uM of MPA.

Example 7

Negative Selection with MTX for K562 Cells

Figure 13:
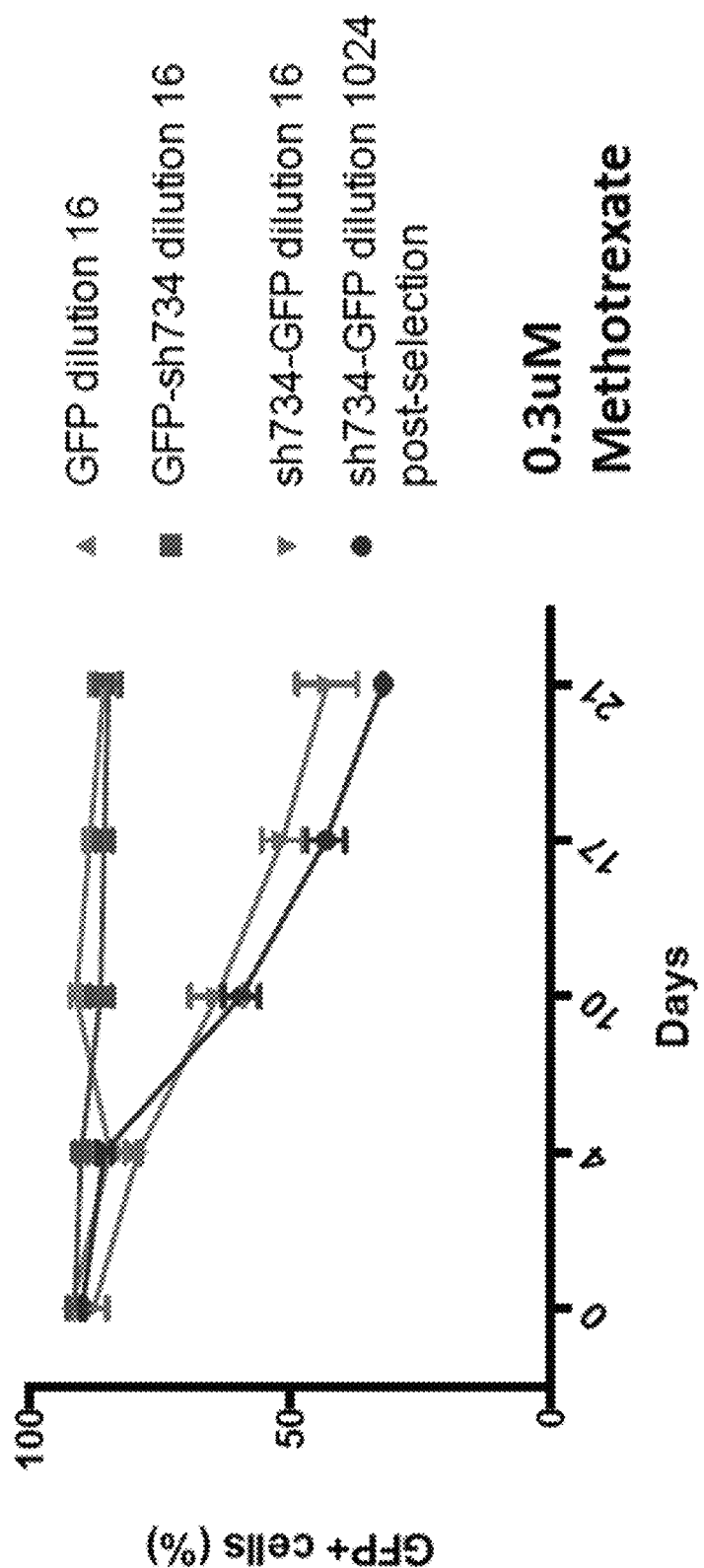
FIG. 13 illustrates the effect of negative selection with MTX on K562 cells.

K562 cells were transduced with either TL20cw-GFP virus soup at dilution factor of 16, TL2Ocw-Ubc/GFP-7SK/sh734 (one sequentially encoding GFP and a shRNA designed to knockdown HPRT) virus soup at dilution factor of 16 and TL2Ocw-7SK/sh734-UBC/GFP (one sequentially encoding a shRNA designed to knockdown HPRT and GFP) virus soup at dilution factor of 16, respectively (see FIG. 13). All cells were cultured with medium containing 0.3 uM of MTX 3 days later. Also shown in FIG. 13 are K562 cells which were transduced by TL20cw-7SK/sh734-UBC/GFP (one encoding a nucleic acid encoding a shRNA designed to knockdown HPRT) virus soup at dilution factor of 1024 one month earlier and where GFP-sh734-transduced cells were positively selected with 300 nM of 6TG 6-TG was selection during that time to reach more than 90% of GFP+ population. As illustrated in FIG. 13, starting from >90% of GFP+ population, GFP or GFP-sh734 transduced cells did not show a reduction in the GFP+ population while the sh734-GFP-transduced cells at high dilution and low dilution levels showed deselection of the GFP+ population. The relative sh734 expression per VCN for sh734-GFP-transduced cells and GFP-sh73-transduced cells were measured. The results suggested that methotrexate could only deselect cells transduced with sh734-high-expression lentiviral vector (TL20cw-7SK/sh734-UBC/GFP) not and not with the sh734-low-expression lentiviral vector (TL20cw-UBC/GFP-7SK/sh734). This example demonstrated that different vector designs (even those having the same shRNA) had an impact on the expression of the shRNA hairpin and could determine whether transduced cells could be deselected or not by MTX.

STATEMENT OF INDUSTRIAL APPLICABILITY

The present disclosure has industrial applicability in the field of medicine, e.g. gene therapy.

Additional Embodiments

Additional Embodiment 1. A method of providing benefits of a lymphocyte infusion while mitigating side effects in a patient comprising (i) administering modified T-cells that are HPRT-deficient to the patient; and (ii) administering MTX to the patient upon an onset of side effects.

Additional Embodiment 2. The method of additional embodiment 1, wherein the side effects are selected from the group consisting of aGVHD or cGVHD.

Additional Embodiment 3. The method of additional embodiment 1, wherein the modified T-cells are administered in a single dose.

Additional Embodiment 4. The method of additional embodiment 3, wherein an amount of modified T-cells administered in the single dose ranges from about $0.1 \times 10^6$ cells/kg body weight to about $730 \times 10^6$ cells/kg body weight.

Additional Embodiment 5. The method of additional embodiment 1, wherein the modified T-cells are administered over multiple doses.

Additional Embodiment 6. The method of additional embodiment 5, wherein an amount of modified T-cells administered per dose ranges from about $0.1 \times 10^6$ cells/kg body weight to about $240 \times 10^6$ cells/kg body weight.

Additional Embodiment 7. The method of additional embodiment 1, wherein the MTX is administered as a single dose.

Additional Embodiment 8. The method of additional embodiment 1, wherein multiple doses of the MTX are administered.

Additional Embodiment 9. The method of additional embodiment 1, wherein an amount of MTX administered ranges from about 2 mg/m$^2$/infusion to about 8 mg/m$^2$/infusion.

Additional Embodiment 10. The method of additional embodiment 9, wherein the amount of MTX administered ranges from about 2.5 mg/m$^2$/infusion to about 7.5 mg/m$^2$/infusion.

Additional Embodiment 11. The method of additional embodiment 1, further comprising (i) monitoring for a reduction in the side effects, and (ii) administering additional modified T-cells that are HPRT-deficient to the patient.

Additional Embodiment 12. A method of inducing a graft versus malignancy effect in a patient following stem cell transplantation comprising (i) administering modified T-cells that are HPRT-deficient to the patient; (ii) monitoring the patient for an onset of side effects; and (iii) administering MTX to the patient upon onset of the side effects.

Additional Embodiment 13. The method of additional embodiment 12, wherein the side effects are selected from the group consisting of aGVHD or cGVHD.

Additional Embodiment 14. The method of additional embodiment 12, wherein the modified T-cells are administered in a single dose.

Additional Embodiment 15. The method of additional embodiment 14, wherein an amount of modified T-cells administered in the single dose ranges from about $0.1 \times 10^6$ cells/kg body weight to about $730 \times 10^6$ cells/kg body weight.

Additional Embodiment 16. The method of additional embodiment 12, wherein the modified T-cells are administered over multiple doses.

Additional Embodiment 17. The method of additional embodiment 16, wherein an amount of modified T-cells administered per dose ranges from about $0.1 \times 10^6$ cells/kg body weight to about $240 \times 10^6$ cells/kg body weight.

Additional Embodiment 18. The method of additional embodiment 12, wherein the MTX is administered as a single dose.

Additional Embodiment 19. The method of additional embodiment 12, wherein multiple doses of the MTX are administered.

Additional Embodiment 20. The method of additional embodiment 12, wherein an amount of MTX administered ranges from about 2 mg/m$^2$/infusion to about 8 mg/m$^2$/infusion.

Additional Embodiment 21. The method of additional embodiment 20, wherein the amount of MTX administered ranges from about 2.5 mg/m$^2$/infusion to about 7.5 mg/m$^2$/infusion.

Additional Embodiment 22. A method of preserving a graft versus malignancy effect while mitigating graft versus host disease in a subject comprising administrating to the subject a therapeutically effective amount of modified T-cells following a stem cell transplant, monitoring the patient for the onset of GVHD, and administering MTX upon onset of GVHD.

Additional Embodiment 23. The method of additional embodiment 22, wherein the graft versus malignancy effect is a graft versus leukemia effect.

Additional Embodiment 24. A method of treating cancer comprising (i) administering a gene-modified adoptive immunotherapy that is HPRT-deficient to a subject in need thereof; (ii) monitoring the subject for an onset of side effects; and (iii) administering MTX upon onset of the side effects.

Additional Embodiment 25. The method of additional embodiment 24, wherein the side effects are selected from the group consisting of aGVHD or cGVHD.

Additional Embodiment 26. The method of additional embodiment 24, wherein the modified T-cells are administered in a single dose.

Additional Embodiment 27. The method of additional embodiment 26, wherein an amount of modified T-cells administered in the single dose ranges from about $0.1 \times 10^6$ cells/kg body weight to about $730 \times 10^6$ cells/kg body weight.

Additional Embodiment 28. The method of additional embodiment 24, wherein the modified T-cells are administered over multiple doses.

Additional Embodiment 29. The method of additional embodiment 28, wherein an amount of modified T-cells administered per dose ranges from about $0.1 \times 10^6$ cells/kg body weight to about $240 \times 10^6$ cells/kg body weight.

Additional Embodiment 30. The method of additional embodiment 24, wherein the MTX is administered as a single dose.

Additional Embodiment 31. The method of additional embodiment 24, wherein multiple doses of the MTX are administered.

Additional Embodiment 32. The method of additional embodiment 24, wherein an amount of MTX administered ranges from about 2 $mg/m^2$/infusion to about 8 $mg/m^2$/infusion.

Additional Embodiment 33. The method of additional embodiment 32, wherein the amount of MTX administered ranges from about 2.5 $mg/m^2$/infusion to about 7.5 $mg/m^2$/infusion.

Additional Embodiment 34. The method of additional embodiment 24, wherein the gene-modified adoptive immunotherapy is selected from the group consisting of CAR-modified cells, autologous and allogenic CAR-modified cells, autologous TCR-modified cells, and allogenic TCR-modified cells.

Additional Embodiment 35. A method of treating a patient with cancer who has received an allogeneic hematopoietic cell transplant, comprising administering to said patient a therapeutically effective amount of modified T-cells, the modified T-cells being HPRT-deficient; monitoring for an onset of side effects resulting from the administration of the modified T-cells; and administering MTX to suppress, reduce, or control the side effect while maintaining a graft-versus malignancy reaction effective to eliminate or reduce the number of cancer cells in the patient.

Additional Embodiment 36. The method of additional embodiment 35, further comprising administering a therapeutically effective amount of a corticosteroid.

Additional Embodiment 37. A method of treating cancer comprising (i) administering to a patient having cancer a therapeutically effective amount of substantially purified modified T-cells, the modified T-cells being HPRT-deficient; and (ii) monitoring the patient for the presence of cancer and for the onset of GVHD, wherein a therapeutically effective amount of MTX is administered upon onset of GVHD.

Additional Embodiment 38. A method of preventing or mitigating post-transplant immune deficiency in a patient following a stem cell transplant, comprising (i) administering modified T-cells that are HPRT-deficient to the patient; (ii) monitoring the patient for an onset of side effects; and (ii) administering MTX to the patient upon the onset of side effects, wherein an amount of the MTX administered ranges from about 2 $mg/m^2$/infusion to about 8 $mg/m^2$/infusion.

Additional Embodiment 39. The method of additional embodiment 38, wherein the MTX is administered in a single dose.

Additional Embodiment 40. The method of additional embodiment 38, wherein multiple doses of MTX are administered.

Additional Embodiment 41. The method of additional embodiment 40, wherein the doses of MTX are titrated.

Additional Embodiment 42. The method of embodiment 38, further comprising administering additional modified T-cells following treatment with MTX.

Additional Embodiment 43. The method of additional embodiment 42, wherein an amount of the additional modified T-cells administered following treatment with MTX ranges from about $0.1 \times 10^6$ cells/kg body weight to about $240 \times 10^6$ cells/kg body weight.

Additional Embodiment 44. A method of enhancing the safety of (i) reconstituting a patient's immune system, or (ii) inducing or maintaining a GVM effect, both following stem cell translation, comprising (a) administering modified T-cells to the patient that are sensitive to MTX; (b) monitoring the patient for an onset of side effects; and (c) administering MTX to the patient upon the onset of the side effects.

Additional Embodiment 45. The method of additional embodiment 44, wherein the modified T-cells that are sensitive to MTX are produced by (i) isolating lymphocytes from cells collected from a donor; (ii) conferring chemoprotection against 6-thioguanine cytotoxicity to at least a portion of the isolated lymphocytes; (iii) selecting for and expanding the portion of the isolated lymphocytes having chemoprotection against 6-thioguanine by contacting the isolated lymphocytes with 6TG.

Additional Embodiment 46. Modified T-cells produced by: (i) isolating lymphocytes from cells collected from a donor; (ii) treating the isolated lymphocytes to provide at least a population of HPRT-deficient cells within the total population of isolated lymphocytes; and (iii) selecting for and expanding the population of HPRT-deficient cells by contacting the total population of isolated lymphocytes with 6TG.

Additional Embodiment 47. The modified T-cells of additional embodiment 46, wherein the step of treating the isolated lymphocytes comprises contacting the isolated lymphocytes with a self-inactivating lentiviral vector encoding a nucleic acid sequence having at least 80% sequence identity to that of SEQ ID NO. 1.

Additional Embodiment 48. The modified T-cells of additional embodiment 46, wherein the step of treating the isolated lymphocytes comprises contacting the isolated lymphocytes with a gene editing tool selected from the group consisting of CRISPR/Cas9 RNP, a zinc-finger protein, TALONS, and ARUCS.

Additional Embodiment 49. A method of providing benefits of a lymphocyte infusion while mitigating side effects in a patient comprising: performing an ex vivo selection, wherein the ex vivo selection comprises treating a population of genetically modified T-cells with 6TG, the genetically modified T-cells being HPRT deficient; administering the ex vivo selected modified T-cells to a patient in need thereof; and performing an in vivo selection, wherein the in vivo selection comprising administering MTX to the patient.

Additional Embodiment 50. The method of additional embodiment 49, wherein the genetically modified T-cells are prepared by treating isolated lymphocytes with a self-inactivating lentiviral vector encoding a nucleic acid sequence having at least 80% sequence identity to that of SEQ ID NO. 1.

Additional Embodiment 51. The method of additional embodiment 49, wherein the genetically modified T-cells are prepared by treating isolated lymphocytes with a gene editing tool selected from the group consisting of CRISPR/Cas9 RNP or a zinc-finger protein.

Additional Embodiment 52. The method of additional embodiment 49, wherein the MTX is administered to the patient following the onset of side effects from treatment with the ex vivo selected modified T-cells.

Additional Embodiment 53. The method of additional embodiment 49, further comprising the step of administering at least one additional dose of ex vivo selected modified T-cells following treatment with MTX.

Additional Embodiment 54. A method of preventing or mitigating post-transplant immune deficiency in a patient following a stem cell transplant, comprising (i) administering modified T-cells that are HPRT-deficient to the patient, wherein an amount of the modified T-cells ranges from about 0.1×106 cells/kg body weight to about 730× 106 cells/kg body weight; (ii) monitoring the patient for an onset of side effects; and (ii) administering MTX to the patient upon the onset of side effects, wherein an amount of the MTX administered ranges from about 2 mg/m2/infusion to about 8 mg/m2/infusion.

Additional Embodiment 55. A method of treating cancer in a patient in need of treatment thereof comprising:
(a) generating CAR-T cells that include an antitumor chimeric receptor and which are HPRT deficient;
(b) positively selecting for the HPRT deficient CAR-T cells ex vivo to provide a population of CAR-T cells for administration; and
(c) administering the population of CAR-T cells to the patient.

Additional Embodiment 56. The method of additional embodiment 55 further comprising administering at least one dose of MTX to suppress at least one symptom of GVHD or CRS.

Additional Embodiment 57. The method of additional embodiment 56, wherein an amount of MTX administered ranges from about 2 mg/m²/infusion to about 100 mg/m²/infusion.

Additional Embodiment 58. The method of additional embodiment 55, wherein the HPRT deficient CAR-T cells are generated through knockdown of the HPRT gene.

Additional Embodiment 59. The method of additional embodiment 55, wherein the positive selection comprises contacting the generated HPRT deficient lymphocytes with both a purine analog and allopurinol.

(d) administering one or more doses of methotrexate or mycophenolic acid if side effects from the administration of the modified lymphocytes arise.

2. The method of claim 1, wherein an amount of methotrexate administered ranges from about 2 mg/m²/infusion to about 100 mg/m²/infusion.

3. The method of claim 1, wherein the methotrexate or mycophenolic acid is administered in titrated doses.

4. The method of claim 1, wherein the positive selection comprises contacting the generated HPRT deficient lymphocytes with a purine analog.

5. The method of claim 4, wherein the purine analog is selected from the group consisting of 6-thioguanine, 6-mercaptopurine, and azathiopurine.

6. The method of claim 5, wherein the purine analog is 6-thioguanine and wherein an amount of 6-thioguanine is between about 1 to about 15 µg/mL.

7. The method of claim 1, wherein the modified lymphocytes are administered as a single bolus.

8. The method of claim 1, wherein multiple doses of the modified lymphocytes are administered.

9. The method of claim 8, wherein each dose comprises between about $0.1 \times 10^6$ cells/kg to about $240 \times 10^6$ cells/kg.

10. The method of claim 9, wherein a total dosage of modified lymphocytes comprises between about $0.1 \times 10^6$ cells/kg to about $730 \times 10^6$ cells/kg.

11. The method of claim 1, wherein the HPRT deficient lymphocytes are generated through knockdown of the HPRT gene, and wherein the knockdown of the HPRT gene comprises contacting lymphocytes with a nucleic acid sequence encoding an shRNA.

12. A method of treating a hematological cancer in a patient in need of treatment thereof comprising:
(a) generating HPRT deficient lymphocytes from a donor sample, wherein the HPRT deficient lymphocytes are generated through knockdown of the HPRT gene;

The invention claimed is:

1. A method of providing benefits of a lymphocyte infusion to a patient in need of treatment thereof comprising:
(a) generating HPRT deficient lymphocytes from a donor sample,
(b) positively selecting for the HPRT deficient lymphocytes ex vivo to provide a population of modified lymphocytes;
(c) administering at least a portion of the population of modified lymphocytes to the patient following an administration of an HSC graft to the patient; and (b) positively selecting for the HPRT deficient lymphocytes ex vivo to provide a population of modified lymphocytes;
(c) inducing at least a partial graft versus malignancy effect by administering an HSC graft to the patient;
(d) administering at least a portion of the population of modified lymphocytes to the patient following the detection of residual disease or disease recurrence; and
(e) administering one or more doses of methotrexate or mycophenolic acid following the administration of the at least the portion of the population of modified lymphocytes if graft versus host disease arises.

13. The method of claim 12, wherein an amount of methotrexate administered ranges from about 2 mg/m$^2$/infusion to about 100 mg/m$^2$/infusion.

14. The method of claim 12, wherein the methotrexate or mycophenolic is administered in titrated doses.

15. The method of claim 12, wherein the positive selection comprises contacting the generated HPRT deficient lymphocytes with a purine analog selected from the group consisting of 6-thioguanine, 6-mercaptopurine, and azathiopurine.

16. The method of claim 12, wherein multiple doses of the modified lymphocytes are administered.

17. The method of claim 16, wherein each dose comprises between about 0.1×10$^6$ cells/kg to about 240×10$^6$ cells/kg.

18. A method of providing benefits of a lymphocyte infusion to a patient in need of treatment thereof comprising:
   (a) generating HPRT deficient lymphocytes from a donor sample, wherein the HPRT deficient lymphocytes are generated through knockdown of the HPRT gene;
   (b) positively selecting for the HPRT deficient lymphocytes ex vivo to provide a population of modified lymphocytes; and
   (c) administering at least a portion of the population of modified lymphocytes to the patient following an administration of an HSC graft to the patient, and
   (d) administering one or more doses of methotrexate or mycophenolic acid if side effects from the administration of the modified lymphocytes arise.

19. The method of claim 18, wherein the knockdown of the HPRT gene comprises contacting lymphocytes with a lentiviral vector comprising a nucleic acid sequence encoding an shRNA.

20. The method of claim 19, wherein the nucleic acid sequence encoding the shRNA has at least 90% identity to SEQ ID NO: 1.

21. The method of claim 19, wherein the nucleic acid sequence encoding the shRNA comprises at least nucleotides 1-46 of SEQ ID NO: 1.

22. The method of claim 19, wherein the nucleic acid sequence encoding the shRNA comprises at least 46 contiguous nucleotides of SEQ ID NO: 1.

23. The method of claim 19, wherein the nucleotide sequence encoding the shRNA is intracellularly processed to generate a siRNA duplex, wherein a first strand of the siRNA duplex comprises nucleotides 2-18 of SEQ ID NO: 1.

24. The method of claim 1, wherein the positive selection comprises contacting the generated HPRT deficient lymphocytes with both a purine analog and allopurinol.

25. The method of claim 11, wherein the contacting of the lymphocytes with the nucleic acid sequence encoding the shRNA comprises contacting the lymphocytes with a lentiviral vector encoding the shRNA.

* * * * *